(12) United States Patent
Wang

(10) Patent No.: US 10,022,877 B2
(45) Date of Patent: Jul. 17, 2018

(54) BENDABLE, TELESCOPIC, AND FLEXIBLE CONTINUUM MECHANICAL STRUCTURE

(71) Applicant: Beijing Surgerii Technology Co., Ltd., Beijing (CN)

(72) Inventor: Wen Wang, Shanghai (CN)

(73) Assignee: Beijing Surgerii Technology Co., Ltd., Beijing (CN)

( * ) Notice: Subject to any disclaimer, the term of this patent is extended or adjusted under 35 U.S.C. 154(b) by 0 days.

(21) Appl. No.: 14/759,643

(22) PCT Filed: Dec. 31, 2013

(86) PCT No.: PCT/CN2013/091151
§ 371 (c)(1),
(2) Date: Jul. 7, 2015

(87) PCT Pub. No.: WO2014/106447
PCT Pub. Date: Jul. 10, 2014

(65) Prior Publication Data
US 2015/0352728 A1    Dec. 10, 2015

(30) Foreign Application Priority Data
Jan. 7, 2013   (CN) .......................... 2013 1 0005269

(51) Int. Cl.
*B25J 18/02* (2006.01)
*A61B 17/00* (2006.01)
(Continued)

(52) U.S. Cl.
CPC ............... *B25J 18/025* (2013.01); *A61B 1/00* (2013.01); *A61B 1/0057* (2013.01);
(Continued)

(58) Field of Classification Search
CPC ................ A61B 1/0056; A61B 1/0057; A61B 17/00234; A61B 2017/00292;
(Continued)

(56) References Cited

U.S. PATENT DOCUMENTS 4,784,042 A * 11/1988 Paynter .................... B25J 9/142
414/7
4,790,624 A * 12/1988 Van Hoye ............ A61B 1/0058
385/118
(Continued)

FOREIGN PATENT DOCUMENTS

CN    101622107 A    1/2010
CN    103085083 A    5/2013
(Continued)

OTHER PUBLICATIONS

ISA State Intellectual Property Office of the People's Republic of China, International Search Report Issued in Application No. PCT/CN2013/091151, dated Mar. 6, 2014, WIPO, 4 pages.

*Primary Examiner* — Victor L MacArthur
*Assistant Examiner* — Joseph H Brown
(74) *Attorney, Agent, or Firm* — McCoy Russell LLP

(57) ABSTRACT

A bendable, telescopic, and flexible mechanical structure comprises: a distal-end structure body, a proximal-end structure body, and a middle connecting body. The distal-end structure body comprises a distal-end spacing disc, a distal-end locking disc and a structure bone. The proximal-end structure body comprises a proximal-end spacing disc, a proximal-end locking disc and the structure bone. The middle connecting body comprises pipe fixing plates and a pipe. The distal-end structure body is connected to the proximal-end structure body through the middle connecting body. One end of the structure bone is fixed on the proximal-end locking disc. Then, the structure bone passes through the
(Continued)

proximal-end spacing disc, the middle connecting body and the distal-end spacing disc sequentially, and is fixed on the distal-end locking disc.

28 Claims, 13 Drawing Sheets

(51) Int. Cl.
```
B25J 9/06      (2006.01)
A61B 1/005     (2006.01)
B25J 18/06     (2006.01)
A61B 1/00      (2006.01)
B25J 9/10      (2006.01)
A61B 34/00     (2016.01)
A61B 34/30     (2016.01)
```
(52) U.S. Cl.
CPC ........ *A61B 17/00234* (2013.01); *A61B 34/70* (2016.02); *B25J 9/065* (2013.01); *B25J 9/104* (2013.01); *B25J 18/06* (2013.01); *A61B 34/71* (2016.02); *A61B 2017/003* (2013.01); *A61B 2017/00292* (2013.01); *A61B 2017/00305* (2013.01); *A61B 2017/00314* (2013.01); *A61B 2017/00323* (2013.01); *A61B 2017/00327* (2013.01); *A61B 2017/00991* (2013.01); *A61B 2034/306* (2016.02); *Y10T 74/20323* (2015.01)

(58) Field of Classification Search
CPC ........... A61B 2017/00305; A61B 2017/00314; A61B 2017/00318; A61B 2017/00323; A61B 2017/00327; A61B 2017/00336; A61B 2034/305; A61B 2034/306; A61B 1/0055; A61B 2017/003; A61B 2017/00991; B25J 18/04; B25J 18/06; B25J 18/025; B25J 9/0015; B25J 9/065; B25J 9/104; B25J 9/1075

USPC .................................................. 74/490.04
See application file for complete search history.

(56) References Cited

U.S. PATENT DOCUMENTS

| | | | | |
|---|---|---|---|---|
| 4,826,087 A * | 5/1989 | Chinery | .............. | B05B 13/0431 137/636 |
| 5,297,443 A * | 3/1994 | Wentz | .................. | B05B 15/066 446/27 |
| 5,317,952 A * | 6/1994 | Immega | .................. | B25J 9/104 74/490.04 |
| 8,827,949 B2 * | 9/2014 | Boulais | ................ | A61B 1/0052 604/528 |
| 8,887,595 B2 * | 11/2014 | Williams | ........... | A61B 19/2203 606/1 |
| 8,911,428 B2 * | 12/2014 | Cooper | ............ | A61B 17/00234 600/101 |
| 9,462,932 B2 * | 10/2016 | Ostrovsky | ............ | A61B 1/0055 |
| 2005/0273084 A1 * | 12/2005 | Hinman | ................ | A61B 1/008 606/1 |
| 2005/0273085 A1 * | 12/2005 | Hinman | ............... | A61B 1/0055 606/1 |
| 2009/0044654 A1 * | 2/2009 | Vaccani | .................... | B25J 9/06 74/490.01 |
| 2010/0234988 A1 * | 9/2010 | Buckingham | ............ | B25J 18/06 700/245 |
| 2010/0261964 A1 * | 10/2010 | Danitz | ................ | A61B 1/0053 600/141 |
| 2010/0324370 A1 * | 12/2010 | Dohi | .................. | A61B 1/00078 600/144 |

FOREIGN PATENT DOCUMENTS

| | | |
|---|---|---|
| CN | 203003905 U | 6/2013 |
| WO | 2009094670 A1 | 7/2009 |
| WO | WO 2009094670 A1 * | 7/2009 ............... A61B 5/11 |

\* cited by examiner

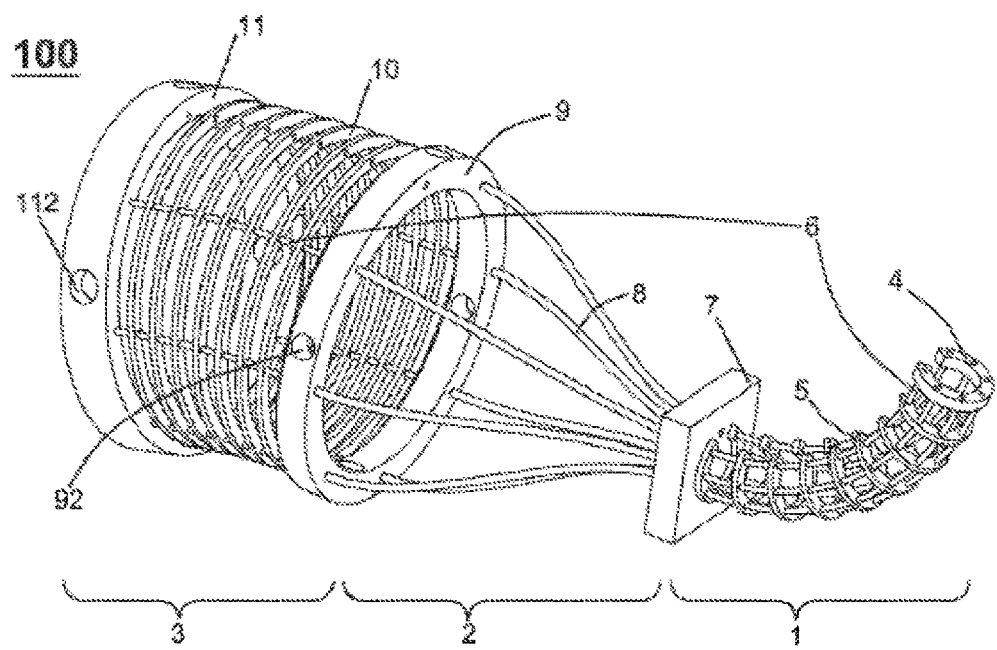
Fig. 3
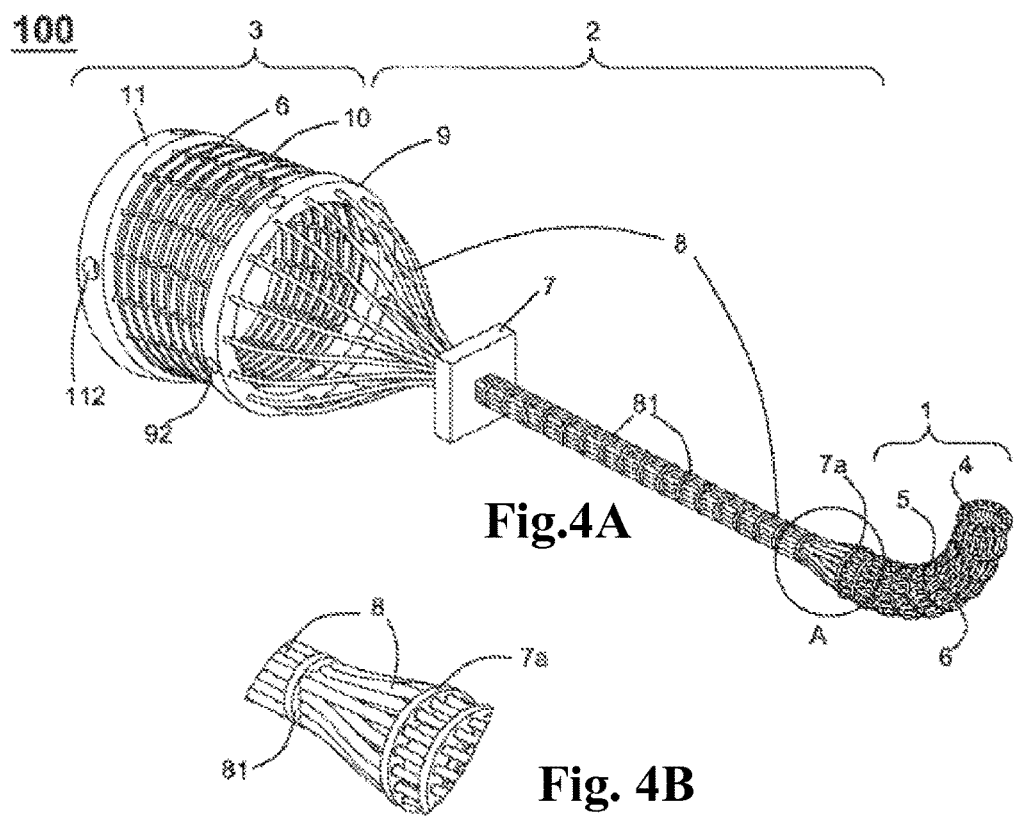
Fig. 4A
Fig. 4B

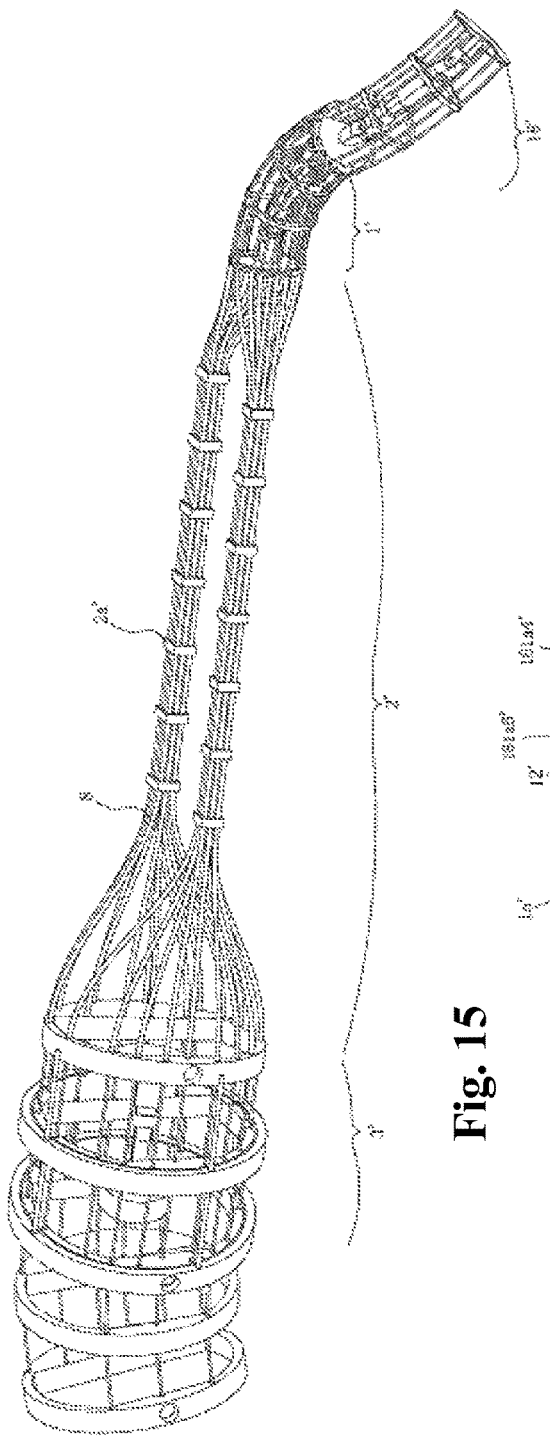
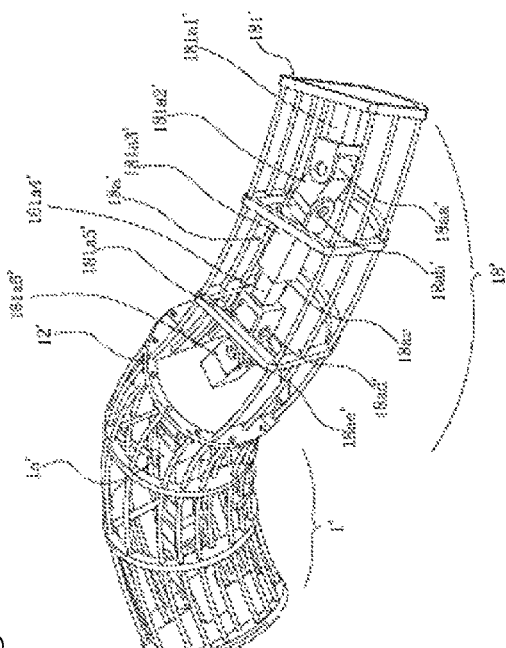
Fig. 15
Fig. 16

BENDABLE, TELESCOPIC, AND FLEXIBLE CONTINUUM MECHANICAL STRUCTURE

CROSS REFERENCE TO RELATED APPLICATIONS

The present application is a U.S. National Phase of International Patent Application Serial No. PCT/CN2013/091151, entitled "BENDABLE, TELESCOPIC, AND FLEXIBLE CONTINUOUS MECHANICAL STRUCTURE," filed Dec. 31, 2013, which claims priority to Chinese Patent Application No. CN201310005269.4, filed Jan. 7, 2013, the entire contents of each of which are hereby incorporated by reference for all purposes.

TECHNICAL FIELD

The present invention relates to the field of medical instruments, industrial automation, etc., in particular to a bendable, telescopic and flexible continuum mechanical structure used for medical instruments, industrial automation devices, etc.

BACKGROUND

In the existing bendable mechanical structures, controllable bending motions are realized basically by two mutually hinged rigid or flexible links through relative rotation at hinged joints. When serial connection of a plurality of independent bending motions is realized through this kind of structure, due to the difficulty in transmission arrangement, generally a drive unit (such as a motor or a hydraulic ejector rod and the like) needs to be installed at each hinged joint and thus distal driving units become the load of proximal drive units, such that the realized structure with this function becomes relatively complex and the size is relatively larger.

In application such as medical surgery or industrial intra-cavity inspection, an extremely small peripheral size is needed for constructing a multi-DOF (degree-of-freedom) and multi-bending-function instrument especially for MIS (minimally invasive surgery) or industrial intra-cavity inspection. Obviously, the previously described solution of realizing the serially connected mechanical structure through a mutual hinged manner has many defects which are difficult to overcome.

SUMMARY

The purpose of the present invention is to provide a mechanical structure, which can be successively connected, bent, extended and retracted, can bear a certain load (torque, external force, etc.) and can realize multi-DOF distal motions through flexible operations with an extremely simple structure.

In order to realize the above-mentioned purpose, the present invention provides a flexible continuum mechanical structure, characterized in that, comprising:

a distal structure, comprising distal spacer discs, a distal locking disc and distal backbones;

a proximal structure, comprising proximal spacer discs, a proximal locking disc and proximal backbones, the distal backbones being fixedly connected with the corresponding proximal backbones or being physically one piece; and a connecting structure, comprising cannulae fixation plates and cannulae, wherein the distal structure is associated with the proximal structure through the connecting structure, one end of the proximal backbone is fixed on the proximal locking disc. Then, the proximal backbone passes through the proximal spacer discs. An opposite end of the proximal backbones is connected with an end of the corresponding distal backbones in the cannulae of the connecting structure. The distal backbones pass through the distal spacer discs, and the opposite end of the distal backbones is fixed on the distal locking disc, such that when the proximal structure is driven to be bent towards any direction, the distal structure is correspondingly bent towards an opposite direction, or when the proximal structure is driven to be extended or retracted, the distal structure is correspondingly retracted or extended.

In a preferred embodiment of the present invention, each of the distal backbones and the corresponding proximal backbone is physically one piece, which is referred to as a backbone hereafter. The backbones protrude into both the distal structure and the proximal structure. Backbones of the distal structure refer to the backbones' portion that are located inside the distal structure, while backbones of the proximal structure refer to the backbones' portion that are located in the proximal structure. The length of the backbones is measurable, estimable or constant.

The present invention further provides another flexible continuum mechanical structure, characterized in that the flexible continuum mechanical structure comprises:

a distal structure, comprising proximal spacer discs, a distal locking disc and backbones of the distal structure;

a proximal structure, comprising proximal spacer discs, a proximal locking disc and backbones of the proximal structure, the backbones of the distal structure being fixedly connected with the corresponding backbones of the proximal structure or being the same backbones on the proximal structure;

a connecting structure, comprising cannulae fixation plates and cannulae; and a driving structure, used for driving the proximal structure to move and consists of a locking disc of the driving structure, spacer disc of the driving structure, driving backbones and a fixation disc of the driving structure, one end of the driving backbones being fixed on the locking disc of the driving structure and sequentially passing through the drive spacer disc and the fixation disc of the driving structure, wherein the distal structure is associated with the proximal structure through the connecting structure, one end of the backbone is fixed on the proximal locking disc and sequentially passes through the proximal spacer discs, the connecting structure and the distal spacer discs, and the other end is fixed on the distal locking disc;

the driving structure is connected with the proximal structure, such that when the driving backbones are driven, the driving structure drives the proximal structure to be bent towards any direction and the distal structure is correspondingly bent towards an opposite direction, or when the driving structure drives the proximal structure to be extended or retracted, the distal structure is correspondingly retracted or extended.

In another preferred embodiment of the present invention, the backbones of the distal structure and the proximal structure consist of elastic thin rods or elastic thin tubes, and the distal locking disc and the distal spacer discs and the proximal locking disc and the proximal spacer discs respectively have the same through hole arrangement and are rigid disc-shaped structures.

In another preferred embodiment of the present invention, a certain distance is kept between the proximal spacer discs and between the proximal spacer discs and the proximal locking disc, and the proximal spacer discs plays the roles of limiting the positions of the backbones and preventing the backbones from buckling under pushing force.

In another preferred embodiment of the present invention, a certain distance is kept between the distal spacer discs and between the distal spacer discs and the distal locking disc, and the distal spacer discs plays the roles of limiting the positions of the backbones and preventing the backbones from buckling under pushing force.

In another preferred embodiment of the present invention, the connecting structure consists of more than three cannulae and more than two cannulae fixation plates, and the backbones of the continuum mechanical structure pass through the cannulae, one end of each backbone reaches into the distal structure, passes through the distal spacer discs and is fixed on the distal locking disc, and the other end of the backbone reaches into the proximal structure, passes through the proximal spacer discs and is fixed on the proximal locking disc.

In another preferred embodiment of the present invention, the flexible continuum mechanical structure is formed by more than two proximal structures and more than two distal structures through successive connection to obtain higher motion dexterity.

In another preferred embodiment of the present invention, the connecting structure has two cannulae fixation plates, the both ends of the cannulae are respectively secured to the two cannulae fixation plates, and the backbones of proximal structures of the continuum mechanical structure can sequentially pass through one of the two cannulae fixation plates, the cannulae and the other cannulae fixation plate and then enter the distal structure.

In another preferred embodiment of the present invention, the proximal structure has one proximal locking disc and a plurality of proximal spacer discs; the distal structure has one distal locking disc and a plurality of distal spacer discs; the proximal structure and the distal structure share a plurality of backbones, and the length of the backbones is measurable, estimable or constant; and one end of the backbones is fixed on the distal locking disc, then sequentially passes through the distal spacer discs, the connecting structure and the proximal spacer discs and then is fixed on the proximal locking disc, such that when the proximal structure is driven to be bent and/or extended and retracted towards any direction, the distal structure is bent and/or extended and retracted towards an opposite direction.

In another preferred embodiment of the present invention, the proximal locking disc is ring-shaped, and a plurality of pin holes along a radial direction are formed in an outer circumferential side of the ring and are used for connecting the proximal structure to a driving structure.

In another preferred embodiment of the present invention, the backbones consist of elastic thin rods or elastic thin tubes, and the number thereof is greater than or equal to three.

In the flexible continuum mechanical structure of the present invention, preferably, the driving structure has one locking disc of the driving structure, a plurality of spacer discs of the driving structure, a plurality of driving backbones and one fixation disc of the driving structure, the locking disc of the driving structure is fixedly connected with the proximal locking disc, and the fixation disc of the driving structure is fixedly connected with the cannulae fixation plates of the connecting structure, such that when the driving structure is driven to be bent and/or extended and retracted towards any direction, the proximal structure is correspondingly bent and/or extended and retracted towards any direction.

In the flexible continuum mechanical structure of the present invention, preferably, the driving backbones consist of elastic thin rods or elastic thin tubes, the number of which is greater than or equal to three, and corresponding pushing and pulling motions of the driving backbones are realized manually or through an automatically controlled electromechanical systems.

In the flexible continuum mechanical structure of the present invention, preferably, the driving structures are successively connected to form a plurality of driving structures to realize driving the continuum mechanical structure formed by a plurality of proximal structures and distal structures through serial connection.

Preferably, the proximal spacer discs and the distal spacer discs are ring-shaped, and a plurality of backbone holes for passing the backbones are formed in the rings.

Preferably, a plurality of pin holes along a radial direction are formed in an outer circumferential side of the cannulae fixation plates, close to the proximal structure, of the connecting structure and are used for connecting the driving structure to the proximal structure.

Preferably, the cannulae have any shape, rigidity or flexibility, but the length of the cannulae should be measurable, estimable or constant.

The present invention further provides another flexible continuum mechanical structure, characterized in that the flexible continuum mechanical structure comprises:

a distal structure, comprising distal spacer discs, a distal locking disc and backbones of the distal structure;

a proximal structure, comprising proximal spacer discs, a proximal locking disc and backbones of the proximal structure, the backbones of the distal structure being fixedly connected with the corresponding backbones of the proximal structure or being the same backbones of the proximal structure; and a connecting structure, comprising more than two fixation plates, a plurality of holes for passing the backbones being formed in the fixation plates, wherein the distal structure is associated with the proximal structure through the connecting structure, one end of the backbone is fixed on the proximal locking disc and sequentially passes through the proximal spacer discs, the connecting structure and the distal spacer discs, and the other end is fixed on the distal locking disc, such that when the proximal structure is driven to be bent towards any direction, the distal structure is correspondingly bent towards an opposite direction, or when the proximal structure is driven to be extended or retracted, the distal structure is correspondingly retracted or extended.

According to another aspect of the present invention, the present invention provides a flexible continuum mechanical structure, characterized in that the flexible continuum mechanical structure comprises:

a distal structure, comprising distal spacers, a distal locking disc and backbones of the distal structure;

distal kinematic chains, built in the distal structure, used for changing the rigidity of the distal structure and kept in kinematic compatibility with the distal structure;

a proximal structure, comprising proximal spacers, a proximal locking disc and backbones of the proximal structure, the backbones of the distal structure being fixedly connected with the corresponding backbones of the proximal structure or being the same backbones on the proximal structure; and a connecting structure, comprising cannulae fixation plates and cannulae, wherein the distal structure is associated with the proximal structure through the connecting structure, one end of the backbone is fixed on the proximal locking disc and sequentially passes through the proximal spacers, the connecting structure and the distal spacers, and the other end is fixed on the distal locking disc, such that when the proximal structure is driven to be bent towards any direction, the distal structure is correspondingly bent towards an opposite direction, or when the proximal structure is driven to be extended or retracted, the distal structure is correspondingly retracted or extended.

According to another aspect of the present invention, the present invention provides a flexible continuum mechanical structure, characterized in that the flexible continuum mechanical structure comprises:

a distal structure, comprising distal spacers, a distal locking disc and backbones; distal kinematic chains, built in the distal structure, used for changing the rigidity of the distal structure and kept in kinematic compatibility with the distal structure;

a proximal structure, comprising proximal spacers, a proximal locking disc and backbones, the backbones of the distal structure being fixedly connected with the corresponding backbones of the proximal structure or being the same backbones on the proximal structure; and a connecting structure, comprising cannulae fixation plates and cannulae, wherein the distal structure is associated with the proximal structure through the connecting structure, one end of the backbone is fixed on the proximal locking disc and sequentially passes through the proximal spacers, the connecting structure and the distal spacers, and the other end is fixed on the distal locking disc, such that when the proximal structure is driven to be bent towards any direction, the distal structure is correspondingly bent towards an opposite direction, or when the proximal structure is driven to be extended or retracted, the distal structure is correspondingly refracted or extended.

In a preferred embodiment, the distal spacers and the proximal spacers are bellows, and holes for passing the backbones are respectively formed in the bellows.

In another preferred embodiment, the distal spacers and the proximal spacers are spiral springs, and holes for passing the backbones are respectively formed in the spiral springs.

Preferably, retaining rings are further arranged on the connecting structure and are used for dividing the cannulae of the connecting structure into a plurality of bundles.

In a preferred embodiment, each distal kinematic chain consists of more than six links; one end of a first link is secured to the distal locking disc or the cannulae fixation plate and the other end is rotatably connected with one end of a second link to form a first rotary joint; the other end of the second link is rotatably connected with one end of a third link to form a second rotary joint; the other end of the third link is retractably connected with one end of a fourth link to form a prismatic joint; the other end of the fourth link is rotatably connected with one end of a fifth link to form a third rotary joint; the other end of the fifth link is rotatably connected with one end of a sixth link to form a fourth rotary joint; the other end of the sixth link is secured to the distal locking disc, or the sixth link is connected to a seventh link and the last link is secured to the distal locking disc; and the arrangement of the rotary joints and the prismatic joint enable the distal kinematic chains to be kept in kinematic compatibility with the distal structure, such that the distal kinematic chains can be bent, extended and retracted towards each direction with the distal structure.

In another preferred embodiment, the distal kinematic chain can comprise a link I, a link II, a link III, a rotary joint arranged between the link I and the cannulae fixation plate or distal locking disc, a prismatic joint arranged between the link I and the link II, a rotary joint arranged between the link II and the link III and a rotary joint arranged between the link III and the distal locking disc.

According to still another aspect of the present invention, the present invention provides a flexible continuum mechanical structure, characterized in that the flexible continuum mechanical structure comprises:

a distal structure, comprising distal spacers, a distal locking disc and backbones of the distal structure;

distal kinematic chains, built in the distal structure, and used for changing the rigidity of the distal structure and kept in kinematic compatibility with the distal structure;

a proximal structure, comprising proximal spacers, a proximal locking disc and backbones of the proximal structure, the backbones on the distal structure being fixedly connected with the corresponding backbones on the proximal structure or being the same backbones on the proximal structure;

a connecting structure, comprising cannulae fixation plates and cannulae; and a driving structure, built in the proximal structure, wherein the distal structure is associated with the proximal structure through the connecting structure, one end of the backbone is fixed on the proximal locking disc and sequentially passes through the proximal spacers, the connecting structure and the distal spacers, and the other end is fixed on the distal locking disc, such that when the proximal structure is bent towards any direction under the actuation of the driving structure, the distal structure is correspondingly bent towards an opposite direction, or when the proximal structure is driven to be extended or retracted, the distal structure is correspondingly retracted or extended.

In a preferred embodiment, the driving structure consists of a plurality of links and a prismatic joint and rotary joints which are arranged between the links and between the links and the proximal locking disc, the prismatic joint can drive the proximal structure to do extension and retraction motions, and the rotary joints can drive the proximal structure to do bending motions.

Preferably, the driving structure comprises a link I, a link II, a link III, a rotary joint arranged between the link I and the cannulae fixation plate, a prismatic joint arranged between the link I and the link II, a rotary joint arranged between the link II and the link III and a rotary joint arranged between the link III and the proximal locking disc, wherein the rotary joint arranged between the link III and the proximal locking disc is a passive rotary joint, and the other rotary joints and the prismatic joint are active joints and both are driven to move by motors so as to drive the proximal structure to do bending motions and/or extension and retraction motions.

The flexible continuum mechanical structure of the present invention realizes the effect of controlling the distal mechanism to be bent and/or extended and retracted towards any direction through proximal operation by using a very simple and compact structure, and has a very wide application range in the medical field and industrial automation equipments.

BRIEF DESCRIPTION OF THE DRAWINGS

FIG. 3 is a stereoscopic view of another variation example of the first embodiment of the flexible continuum mechanical structure of the present invention;

FIGS. 4A-4B are stereoscopic views of another variation examples of the first embodiment of the flexible continuum mechanical structure of the present invention, wherein FIG. 4B is a locally enlarged view of part A in FIG. 4A;

FIGS. 11A and 11B are another structural schematic views of the two ring-section continuum mechanical structures of the present invention, wherein FIG. 11B is a locally enlarged view of part B in FIG. 11A;

FIG. 15 is a stereoscopic view of the third embodiment of the flexible continuum mechanical structure of the present invention;

FIG. 16 is a stereoscopic view of a distal structure in FIG. 15;

DETAILED DESCRIPTIONS

Figure 1:
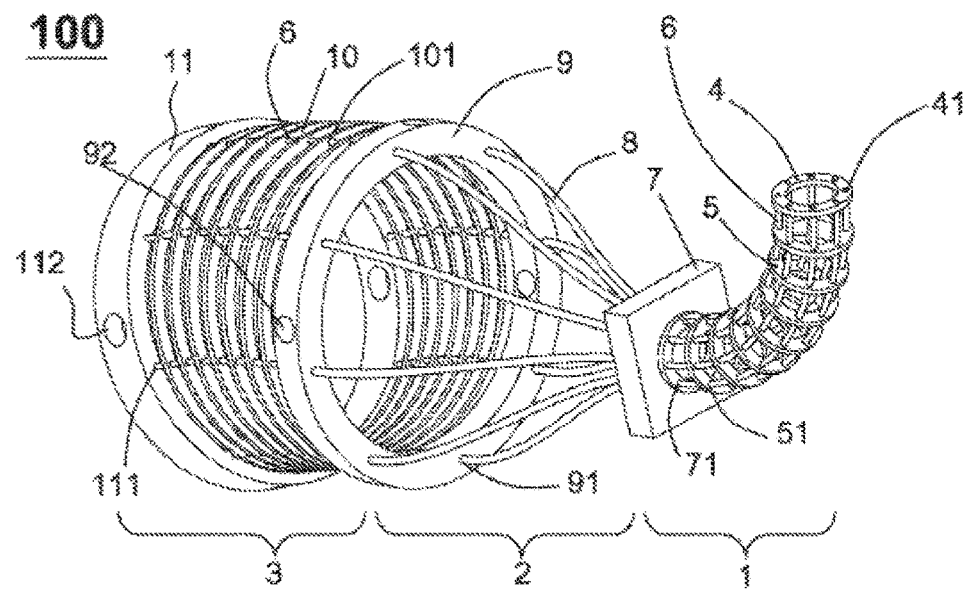
FIG. 1 is a stereoscopic view of the first embodiment of the flexible continuum mechanical structure of the present invention.

The preferred embodiments of the present invention will be described below in details in combination with the drawings, so as to more clearly understand the purposes, features and advantages of the present invention. It should be understood that the embodiments illustrated by the drawings are used for describing the substantive spirit of the technical solution of the present invention instead of limiting the range of the present invention. In the description, the same drawing reference signs represent the same or similar parts.

The present invention provides a serially connectable, bendable and telescopic flexible continuum mechanical structure, which can achieve controllable bending, extension and retraction motions, has a certain load bearing capacity and can also realize serial connection of a plurality of bending, extension and retraction motions in a serial connection manner. A driving structure of the mechanical structure can be separated from the flexible continuum mechanical structure, so as to realize the effects that the driving structure is replaceable and one driving structure can drive a plurality of the flexible continuum mechanical structures.

Specifically, the flexible continuum mechanical structure consists of a distal structure, a proximal structure and a connecting structure. The distal structure is associated with the proximal structure through the connecting structure. The distal structure consists of distal spacer discs, a distal locking disc and backbones. The proximal structure consists of proximal spacer discs, a proximal locking disc and backbones. The connecting structure consists of cannulae (preferably rigid cannulae) and cannulae fixation plates.

A driving structure can be connected with the proximal structure and can drive the proximal structure. Under the actuation of the driving structure, the proximal structure can be bent and/or extended and retracted towards any direction, such that the distal structure is driven to be bent and/or extended and retracted towards any direction.

The backbones in the distal structure consists of elastic thin rods or elastic thin tubes and can bear pulling force or pushing force, the number and distribution of which can be set according to the demands. The distal locking disc and the distal spacer discs are rigid disc structures and have the same through hole arrangement, the diameter of holes in the distal spacer discs is slightly larger than the outer diameter of the backbones to ensure that the backbones can freely pass through the holes, and the diameter of partial or all holes in the distal locking disc is slightly smaller than the outer diameter of the backbones such that partial or all backbones cannot slide relative to the locking disc, or partial or all backbones can also be locked onto the distal locking disc through additional locking devices. The shapes of the distal locking disc and the distal spacer discs and the arrangement of holes thereon can be customized according to design demands (As a simple example, the distal locking disc and the distal spacer discs are circular-ring-shaped structures and a plurality of through holes are uniformly distributed along a circumferential direction). A certain distance is maintained between the spacer discs and between the spacer discs and the locking disc, and the spacer discs play the roles of limiting the positions of the backbones and preventing the backbones from buckling under pushing force.

The backbones in the proximal structure also consists of elastic thin rods or elastic thin tubes and can bear pulling force or pushing force, the number and distribution of which can be set according to the demands. The proximal locking disc and the proximal spacer discs are rigid disc structures and have the same through hole arrangement, the diameter of holes in the proximal spacer discs is slightly larger than the outer diameter of the backbones to ensure that the backbones can freely pass through the holes, and the diameter of partial or all holes in the proximal locking disc is slightly smaller than the outer diameter of the backbones such that partial or all backbones cannot slide relative to the locking disc. The shapes of the proximal locking disc and the proximal spacer discs and the arrangement of holes thereon can be set according to design demands (For a simple example, the proximal locking disc and the proximal spacer discs are circular-ring-shaped structures and a plurality of through holes are uniformly distributed along a circumferential direction). A certain distance is kept between the spacer discs of the proximal structure and between the spacer discs and the locking disc, and the spacer discs play the roles of limiting the positions of the backbones and preventing the backbones from buckling under pushing force.

The cannulae in the connecting structure are fixed by two or more cannulae fixation plates. The shape, direction, length, bending situation and offsets of the cannulae can be set freely. The number of the cannulae can be determined according to the number of the distal backbones and the proximal backbones. The backbones continuously pass through the cannulae in the connecting structure; one end of the backbones reaches into the distal structure, passes through the distal spacer discs and is fixed on the distal locking disc; and the other end of the backbones reaches into the proximal structure, passes through the proximal spacer discs and is fixed on the proximal locking disc.

When the connecting structure is kept to be fixed, since the length of each backbones is measurable, estimable or constant, bending the proximal structure will enable the distal structure to be bent towards an opposite direction, and any bending of the distal structure can always be realized through the corresponding bending of the proximal structure. The proximal structure can also change the length thereof to be increased through actuation, the length of the distal structure will be correspondingly shortened, and vice versa. In general, the bending, extension and retraction of the distal structure towards any direction can be realized through the corresponding actuation of the proximal structure. The peripheral size of the distal structure can be larger, smaller or similar to that of the proximal structure, so as to satisfy performance demands in different scenarios.

Such flexible continuum mechanical structures can be sequentially and serially connected to form a plurality of continuum mechanical structures, i.e., a plurality of proximal structures and/or a plurality of distal structures can be sequentially and serially connected. For example, two proximal structures and two distal structures can be sequentially and successively connected, wherein the proximal structure and the distal structure in the middle form the first continuum mechanical structure, the proximal structure and the distal structure at the two ends form the second continuum mechanical structure, and the first continuum mechanical structure and the second continuum mechanical structure share one connecting structure. Backbones of the second continuum mechanical structure are firstly and fixedly connected with the distal locking disc of the second continuum mechanical structure, pass through the distal spacer discs of the second continuum mechanical structure, then sequentially pass through the distal structure of the first continuum mechanical structure, the cannulae in the shared connecting structure and the proximal structure of the first continuum mechanical structure, pass through the proximal spacer discs of the second continuum mechanical structure and are fixedly secured to the proximal locking disc of the second continuum mechanical structure. If the backbones in the first continuum mechanical structure are thin tubes, the backbones in the second continuum mechanical structure can concentrically pass through the backbones of the first continuum mechanical structure and then are connected into the distal structure and the proximal structure of the second continuum mechanical structure. The backbones of the second continuum mechanical structure can also be not in a relative motion relation with the first continuum mechanical structure, directly pass through the shared connecting structure and then are connected into the distal structure and the proximal structure of the second continuum mechanical structure. The free bending, extension and retraction of the distal structures of the two continuum mechanical structures can be realized by driving the proximal structures of the two continuum mechanical structures. Similarly, a plurality of continuum mechanical structures can be successively connected to realize the serial connection of a plurality of bending, extension and retraction motions, so as to obtain higher motion dexterity. High-strength backbones (for example, made from nickel-titanium alloy or stainless steel) can enable the structure to realize dexterous motion and simultaneously have a load bearing capacity, the capacity is determined by factors such as the diameter, material, number, distribution and length of the backbones in the continuum mechanical structures, the capacity can also be adjusted by controlling related parameters of the backbones and the spacer discs in the continuum mechanical structures, and thus a higher load bearing capacity or a lower load bearing capacity (with easier deformation under external forces to better adapt surrounding environments) can be realized.

In the driving structure which is used for actuating the continuum mechanical structure, the driving structure can be separated from the continuum mechanical structure, so as to realize the effects that the driving structure is replaceable and one driving structure can drive a plurality of continuum mechanical structures. The driving structure consists of a locking disc of the driving structure, spacer discs of the driving structure, driving backbones and a fixation disc of the driving structure.

The driving backbones consist of elastic thin rods or elastic thin tubes and can bear pulling force or pushing force, the number of which must be greater than or equal to three, and the corresponding pushing and pulling motions of the driving backbones may be realized manually or through an automatically controlled electromechanical system. The locking disc of the driving structure and the spacer discs of the driving structure are rigid structures (the shape thereof can be circular or non-circular) and have the same through hole arrangement, the diameter of holes in the spacer discs of the driving structure is slightly larger than the outer diameter of the driving backbones to guarantee that the driving backbones can freely pass through the holes, and the diameter of partial or all holes in the locking disc of the driving structure is slightly smaller than the outer diameter of the driving backbones such that partial or all driving backbones cannot slide relative to the locking disc of the driving structure.

Large through holes are formed in the locking disc of the driving structure and the fixation disc of the driving structure and can allow the proximal structure of the continuum mechanical structure to pass. The locking disc of the driving structure and the fixation disc of the driving structure can also be respectively connected with the proximal locking disc in the continuum mechanism structure and the cannulae fixation plates of the connecting structure through pins. The collaborative pushing and pulling motions of the driving backbones can achieve the free bending, extension and retraction of the driving structure, the motion of the locking disc of the driving structure in the driving structure can drive the proximal locking disc in the continuum mechanical structure to move, thus the free bending, extension and retraction of the proximal structure are realized and finally the bending, extension and retraction of the distal structure are realized.

The driving structures can also be serially connected to form a plurality of driving structures to drive the serially connected continuum mechanical structure. For example, when two proximal structures and two distal structures are serially connected to form the continuum mechanical structures, correspondingly, two driving structures can be arranged. After the serial connection, the driving backbones of the second driving structure are fixedly connected to the locking disc of the driving structure of the second driving structure, pass through the spacer discs of the driving structure of the second driving structure, then pass through the locking disc of the driving structure and the spacer discs of the driving structure of the first driving structure and are driven manually or electromechanically, so as to realize the bending, extension and retraction of the second driving structure, drive the proximal structure of the second continuum mechanical structure to be bent, extended and retracted, and finally realize the bending, extension and retraction of the distal structure of the second continuum mechanical structure.

Embodiment 1

FIG. 1 illustrates a stereoscopic view of the first embodiment of the flexible continuum mechanical structure according to the present invention. As shown in FIG. 1, the flexible continuum mechanical structure 100 consists of a distal structure 1, a connecting structure 2 and a proximal structure 3. The distal structure 1 comprises a distal locking disc 4, distal spacer discs 5 and backbones 6. The connecting structure 2 comprises cannulae fixation plates 7, 9 and cannulae 8. The proximal structure 3 comprises proximal spacer discs 10, a proximal locking disc 11 and backbones 6. In this embodiment, the backbones 6 on the distal structure 1 and the corresponding backbones 6 on the proximal structure are the same backbones. However, one skilled in the art will understand that the backbones on the distal structure 1 and the corresponding backbones 6 on the proximal structure can also be not the same backbones but are fixedly connected together through various connecting structures. The backbones 6 are locked onto the distal locking disc 4, pass through the distal spacer discs 5, the cannulae 8 and the proximal spacer discs 10, and are locked onto the proximal locking disc 11. The length of the backbones 6 in the continuum mechanical structure is measurable and estimable or can be kept to be constant. Pin holes 112 and 92 for connecting with the driving structure are formed in the proximal locking disc 11 and the cannulae fixation plates 9.

Specifically, the distal structure 1 has one distal locking disc 4, a plurality of distal spacer discs 5 and a plurality of backbones 6. The number of the distal spacer discs can be set according to the length of the distal structure as required, the number of the backbones can be set according to the load and compliance which need to be realized, and in the embodiment as shown in FIG. 1, eight backbones 6 are arranged and 3, 4, 5, 6 ... 19, 20 ... backbones can also be arranged. The backbones can be elastic thin rods or elastic thin tubes. The distal locking disc 4 and the distal spacer discs 5 may have any suitable ring or half-ring shape. In the embodiment as shown in FIG. 1, the distal locking disc 4 is circular-ring-shaped, a plurality of backbone locking holes 41 used for locking the backbones 6 are formed thereon, and the diameter of the backbone locking holes 41 is slightly smaller than the diameter of the backbones. The shape of the distal spacer discs 5 is the same as the shape of the distal locking disc 4, and the diameter of backbone holes 51 thereon is slightly larger than the diameter of the backbones 6 to allow the backbones 6 to freely pass through the distal spacer discs 5. During assembling, elastic sleeves can be arranged on the surfaces of the backbones 6 and between the spacer discs 5, or the outer circumference of the spacer discs 5 can be wrapped with a layer of elastic sleeve to enable the spacer discs 5 to be always uniformly distributed and simultaneously allow the backbones 6 to slide relative to the spacer discs 5.

The proximal structure 3 has one proximal locking disc 11, a plurality of proximal spacer discs 10 and a plurality of backbones 6. The number of the proximal spacer discs is set according to the length of the proximal structure as required, and the number of the backbones is determined by the number of the backbones in the distal structure. Eight backbones 6 are arranged in the embodiment as shown in FIG. 1. The proximal locking disc 11 and the proximal spacer discs 10 may have any suitable ring or half-ring shape. In the embodiment as shown in FIG. 1, the proximal locking disc 11 is circular-ring-shaped, backbone fixation holes 111 used for fixing the backbones 6 are formed thereon, and the backbones 6 can be fixed on the backbone fixation holes 111 through bonding, welding or press fit. Or, a clamping mechanism can be arranged on the proximal locking disc, so as to clamp and fix the backbones 6 on the proximal locking disc 11. Four pin holes 112 (a suitable number of pin holes 112 can be arranged according to the needs) along the radial direction are further formed in the outer circumferential side of the proximal locking disc 11 and are used for connecting with the driving structure, which will be described below in more details. The shape of the proximal spacer discs 10 is substantially the same as the shape of the proximal locking disc 11, and the diameter of backbone holes 101 thereon is slightly larger than the diameter of the backbones 6, so as to allow the backbones 6 to freely pass through the proximal spacer discs 10. During assembling, elastic sleeves can be arranged on the surfaces of the backbones 6 and between the spacer discs 10, or the outer circumference of the spacer discs 10 can be wrapped with a layer of elastic sleeve to enable the spacer discs 10 to be always uniformly distributed and simultaneously allow the backbones 6 to slide relative to the spacer discs 10.

The connecting structure 2 comprises a cannulae fixation plate 7 which is connected with the distal structure 1, cannulae 8 and a cannulae fixation plate 9 which is connected with the proximal structure 3. The cannulae fixation plate 7 and the cannulae fixation plate 9 can be any suitable structures in which holes for allowing the passing of the cannulae 8 and the backbones are formed. In the embodiment as shown in FIG. 1, the cannulae fixation plate 7 is a rectangular plate part, the middle part of which is provided with eight through holes 71 which allow the passing of the cannulae 8 and are distributed at intervals at equal angles. The cannulae fixation plate 9 is a circular ring part, which thereon is provided with eight through holes 91 which allow the passing of the cannulae 8 and are distributed at intervals at equal angles. Four pin holes 92 (a suitable number of pin holes 92 may be arranged according to the needs) along the radial direction are further formed in the outer circumferential side of the cannulae fixation plate 9 and are used for connecting with the driving structure. The two ends of the cannulae 8 are connected with through holes 71, 91 in the cannulae fixation plate 7 and the cannulae fixation plate 9 through welding, connection or press fit, respectively. In needs to be pointed out that the shape, direction, length, bending situation and offsets of the cannulae 8 can be freely set. As shown in FIG. 4A, the section area occupied by the cannulae 8 after being constrained can even be smaller than that of the distal structure 1 or the proximal structure 3, which will be described below in more details. In addition, if the cannulae fixation plate 7 and the cannulae fixation plate 9 are fixed during use, the cannulae 8 can be canceled and a plurality of holes for the passing of the backbones are formed in the cannulae fixation plate 7 and the cannulae fixation plate 9.

After completion of assembling, one end of the backbones 6 is fixed on the distal locking disc 4, sequentially pass through the distal spacer discs 5, the cannulae fixation plate 7, the cannulae 8, the cannulae fixation plate 9 and the proximal spacer discs 10, and are finally locked onto the proximal locking disc 11. When the driving structure (not shown in FIG. 1) is driven by motors or manually to be bent and/or extended and refracted towards any direction, the proximal structure 3 is correspondingly bent, extended and retracted towards any direction. Since the length of the backbones 6 is measurable, estimable or constant, the distal structure is also correspondingly bent, extended and refracted towards any direction, which will be described below in more details.

Figure 2:
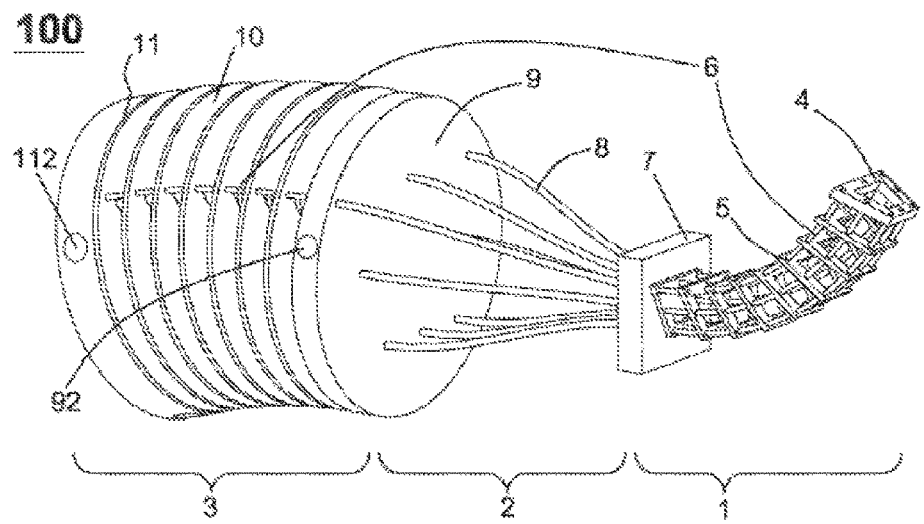
FIG. 2 is a stereoscopic view of a variation example of the first embodiment of the flexible continuum mechanical structure of the present invention.

FIGS. 2-4B illustrate three variation examples of the first embodiment of the flexible continuum mechanical structure according to the present invention. The variation example as shown in FIG. 2 and the flexible continuum mechanical structure as shown in FIG. 1 are different in the shapes of the distal locking disc and the distal spacer discs of the distal structure, the spacer discs of the proximal structure and the cannulae fixation plates of the connecting structure, wherein the distal locking disc 4 and the distal spacer discs 5 are rectangular-ring-shaped, the sections of which are polygon and backbone holes for passing the backbones 6 are formed in each sides of the polygon. The cannulae fixation plate 9 of the connecting structure is disc-shaped.

The variation example as shown in FIG. 3 and the flexible continuum mechanical structure as shown in FIG. 1 are different in the shapes of the distal locking disc and the distal spacer discs of the distal structure. In this embodiment, the shape of the sections of the distal locking disc and the distal spacer discs is a ring shape with a notch or is called as an arc shape. Other parts are the same, which are not described in details herein.

The variation examples as shown in FIGS. 4A-4B and the flexible continuum mechanical structure as shown in FIG. 1 are different in the structure of the connecting structure. As shown in FIG. 4A and FIG. 4B, the connecting structure 2 can be extended for a certain distance from the cannulae fixation plate 7 on the basis of the embodiment as shown in FIG. 1, and a plurality of cannulae fixation discs 81 and one cannulae fixation plate 7a are correspondingly added. Therefore, the length of the connecting structure can be elongated and the shape of the connecting structure can be changed to satisfy different demands. The shape of the cannulae fixation discs and the arrangement of cannulae holes thereof can be arranged according to the needs to satisfy different demands. In the embodiment as shown in FIG. 4A, the cannulae fixation discs 81 are circular-ring-shaped and the cannulae holes thereon are arranged in four columns and four rows. However, one skilled in the art should understand that the cannulae fixation discs with any shape can be designed and the cannulae holes can be freely arranged according to the needs.

Figure 5:
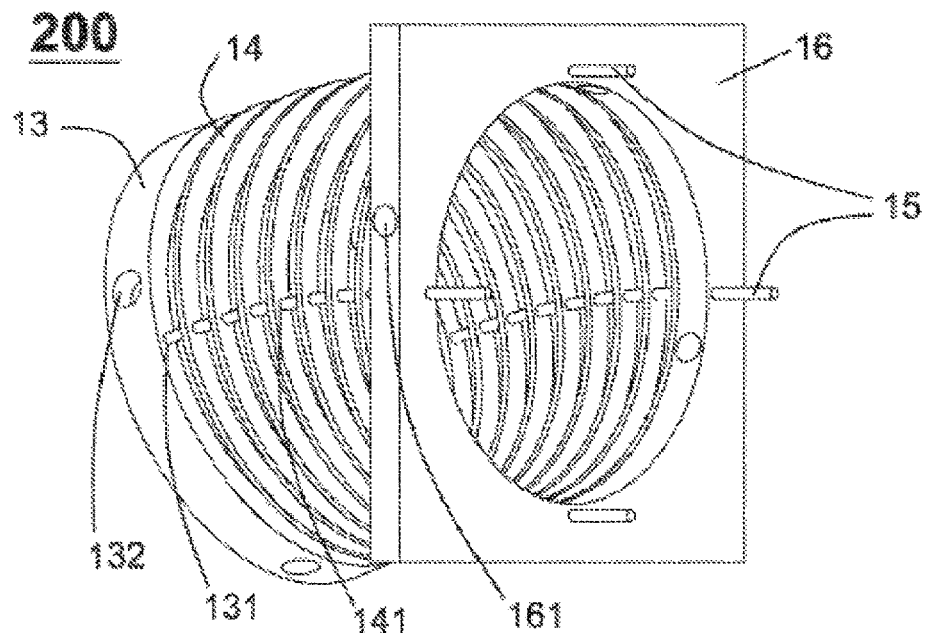
FIG. 5 is a structural schematic view of the first embodiment of a driving structure of the continuum mechanical structure of the present invention.
Figure 6:
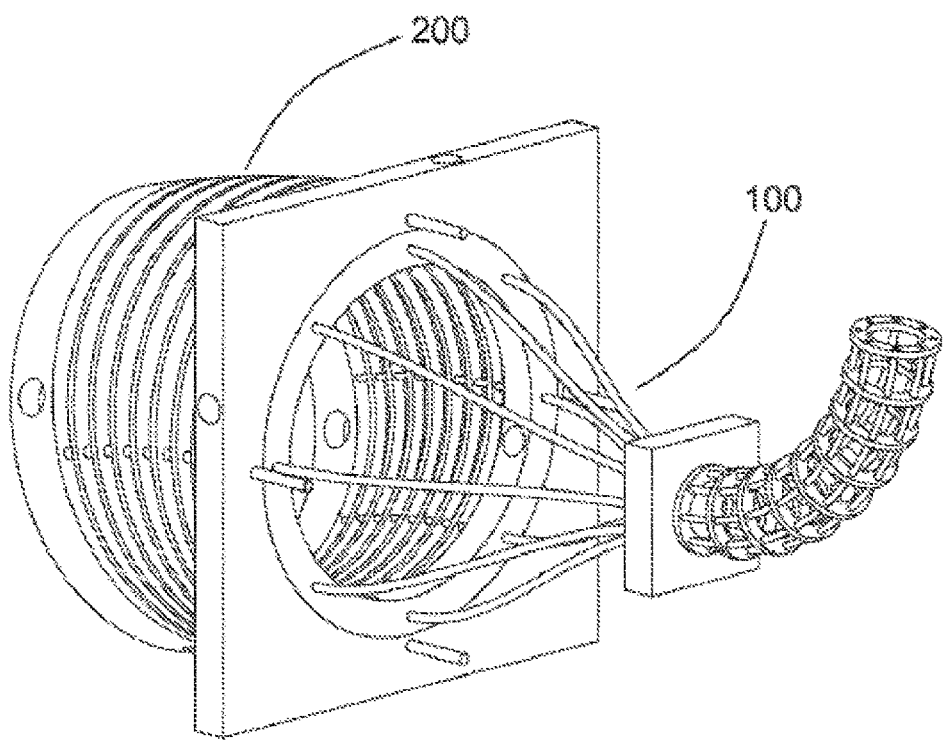
FIG. 6 is a structural schematic view of a circular-ring-section continuum mechanical structure of the present invention after being assembled to the driving structure.
Figure 7:
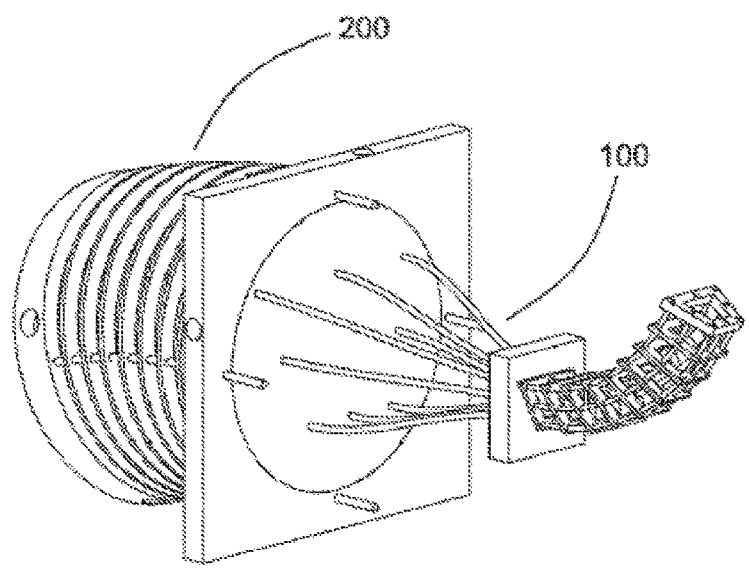
FIG. 7 is a structural schematic view of a square-ring-section continuum mechanical structure of the present invention after being assembled to the driving structure.
Figure 8:
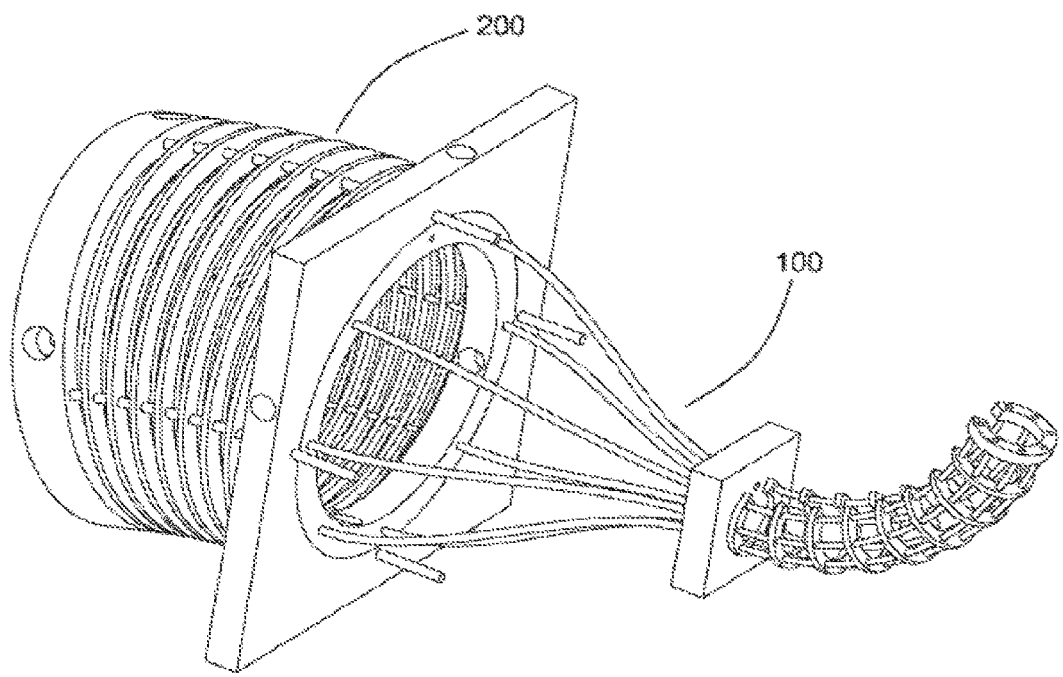
FIG. 8 is a structural schematic view of an incomplete ring-section continuum mechanical structure of the present invention after being assembled to the driving structure.
Figure 9:
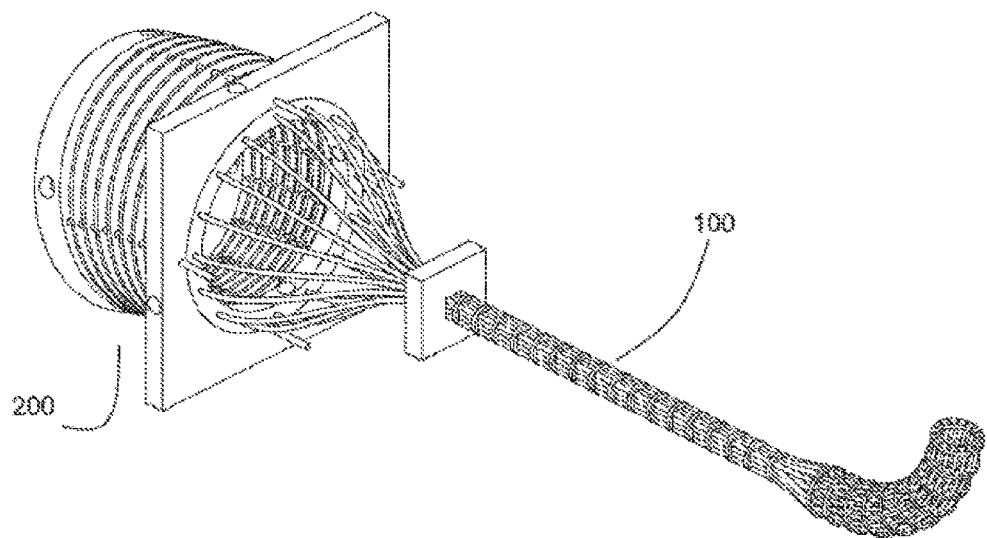
FIG. 9 is a structural schematic view of a middle-constrained ring-section continuum mechanical structure of the present invention after being assembled to the driving structure.

FIG. 5 illustrates a structural schematic view of the first embodiment of a driving structure 200 of the flexible continuum mechanical structure according to the present invention. As shown in FIG. 5, the driving structure of the flexible continuum mechanical structure consists of a locking disc of the driving structure 13, spacer discs of the driving structure 14, driving backbones 15 and a fixation disc of the driving structure 16. The driving backbones 15 are fixed on the locking disc of the driving structure 13 and can freely pass through the spacer discs of the driving structure 14 and the fixation disc of the driving structure 16. The driving backbones 15 are actuated through the linear motion realized by motors or pushing and pulling manually, and the motion combination of the driving backbones 15 can bend, extend and retract the driving structure towards any direction. Pin holes 132 and 161 used for connecting with the proximal locking disc 11 and the cannulae fixation plate 9 are respectively formed in the locking disc of the driving structure 13 and the fixation disc of the driving structure 16.

Specifically, the driving structure has one locking disc of the driving structure 13, a plurality of spacer discs of the driving structure 14, a plurality of driving backbones 15 and one fixation disc of the driving structure 16. After assembling, the driving structure forms a through hole along an axial direction thereof to hold the proximal structure 3. The number of the spacer discs of the driving structure is set according to the length of the proximal structure, the number of the driving backbones 15 is set according to a load which needs to be realized but at least three driving backbones 15 are needed, and in the embodiment as shown in FIG. 5, four driving backbones 15 are arranged. The locking disc of the driving structure 13 and the spacer discs of the driving structure 14 may have any suitable shape which is matched with the proximal structure. In the embodiment as shown in FIG. 5, the locking disc of the driving structure 13 is circular-ring-shaped, backbone fixation holes 131 used for fixing the driving backbones 15 are formed thereon, and the driving backbones 15 can be fixed in the backbone fixation holes 131 through bonding, welding or interference fit. Or, a clamping mechanism can also be arranged on the locking disc of the driving structure to clamp and fix the driving backbones 15 in the locking disc of the driving structure 13. Four pin holes 132 (a suitable number of pin holes 132 can be arranged according to the needs) are further formed in the outer circumferential side of the locking disc of the driving structure 13 and are used for connecting with the proximal structure. The shape of the spacer discs of the driving structure 14 is substantially the same as the shape of the proximal spacer discs 10, and the diameter of driving backbone holes 141 thereon is slightly larger than the diameter of the driving backbones 15, so as to allow the driving backbones 15 to freely pass through the spacer discs of the driving structure 14. During assembling, elastic sleeves can be arranged on the surfaces of the driving backbones 15 and between the spacer discs of the driving structure 14, or the outer circumference of the spacer discs of the driving structure 14 can be wrapped with a layer of elastic sleeve to enable the spacer discs 14 to be always uniformly distributed and simultaneously allow the driving backbones 15 to slide relative to the spacer discs of the driving structure 14.

FIGS. 6-9 respectively illustrate a structural view of the flexible continuum mechanical structure 100 in FIGS. 1-4B after being assembled to the driving structure 200 in FIG. 5. As shown in FIGS. 6-9, the proximal structure 3 is held in the through hole formed by the driving structure and is respectively connected with the pin holes 132 and 161 in the driving structure through the pin holes 112 and 92 in the proximal structure (through pins, etc.), such that the flexible continuum mechanical structure 100 is assembled on the driving structure 200, wherein the proximal locking disc 11 is fixedly connected with the locking disc of the driving structure 13 and the cannulae fixation plate 9 is fixedly connected with the fixation disc of the driving structure 16.

After assembling, the synchronized pushing and pulling of the driving backbones 15 can enable the locking disc of the driving structure 13 to be bent towards any direction and can simultaneously enable the entire length of the driving structure to be lengthened and shortened. Since the locking disc of the driving structure 13 and the fixation disc of the driving structure 16 are respectively connected with the proximal locking disc 11 and the cannulae fixation plate 9 through pins, the synchronized pushing and pulling of the driving backbones 15 enables the proximal structure 3 to be bent, extended and retracted towards any direction, such that the bending, extension and retraction of the distal structure 1 towards any direction are realized.

Embodiment 2

Figure 10:
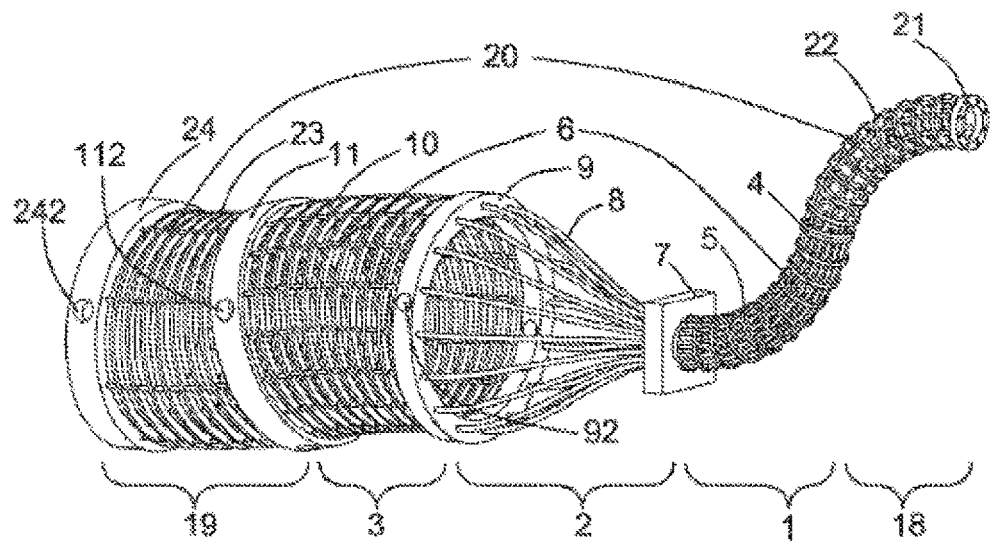
FIG. 10 is a structural schematic view of two ring-section continuum mechanical structures of the present invention.

FIG. 10 illustrates a structural view of the second embodiment of the flexible continuum mechanical structure according to the present invention. In this embodiment, the flexible continuum mechanical structures can be sequentially and successively connected to form a plurality of continuum mechanical structure, i.e., a plurality of proximal structures and/or a plurality of distal structures can be sequentially and successively connected. In the embodiment as shown in FIG. 10, two proximal structures and two distal structures are serially connected and share one connecting structure, wherein the basic structures of each proximal structures, each distal structures and the connecting structure are the same as that in the embodiment as shown in FIG. 1, which are not described herein in details.

As shown in FIG. 10, the first proximal structure 3 and the first distal structure 1 form the first continuum mechanical structure, while the second proximal structure 19 and the second distal structure 18 form the second continuum mechanical structure. The distal structure 18 of the second continuum mechanical structure may be serially connected to the distal structure 1 of the first continuum mechanical structure, while the proximal structure 19 of the second continuum mechanical structure is serially connected to the proximal structure 3 of the first continuum mechanical structure. Backbones 20 of the second continuum mechanical structure firstly and fixedly connected with a distal locking disc 21 of the second continuum mechanical structure, pass through the distal spacer discs 22 of the second continuum mechanical structure, then sequentially pass through the distal structure 1 (including the first distal locking disc 4 and the first distal spacer discs 5) of the first continuum mechanical structure, cannulae 8 (the number of the cannulae 8 is greater than or equal to the total number of the number of backbones 6 of the first continuum mechanical structure plus the number of backbones 20 of the second continuum mechanical structure) in the shared connecting structure 2 and the proximal structure 3 of the first continuum mechanical structure (including a proximal locking disc 11 and proximal spacer discs 10 of the first continuum mechanical structure), pass through the proximal spacer discs 23 of the second continuum mechanical structure and are fixedly connected onto a proximal locking disc 24 of the second continuum mechanical structure. At this moment, through holes are formed at corresponding positions on the distal locking disc 4 and the proximal locking disc 11 of the first continuum mechanical structure, and the backbones of the second continuum mechanical structure can freely pass through the through holes. Pin holes 242, 112 and 92 used for connecting with a driving structure are formed in the proximal locking disc 24 of the second continuum mechanical structure, the proximal locking disc 11 of the first continuum mechanical structure and a cannulae fixation plate 9. In addition, according to the requirements, any number of proximal structures and any number of distal structures can be arranged to realize different extension, refraction and bending motions.

Figure 11A:
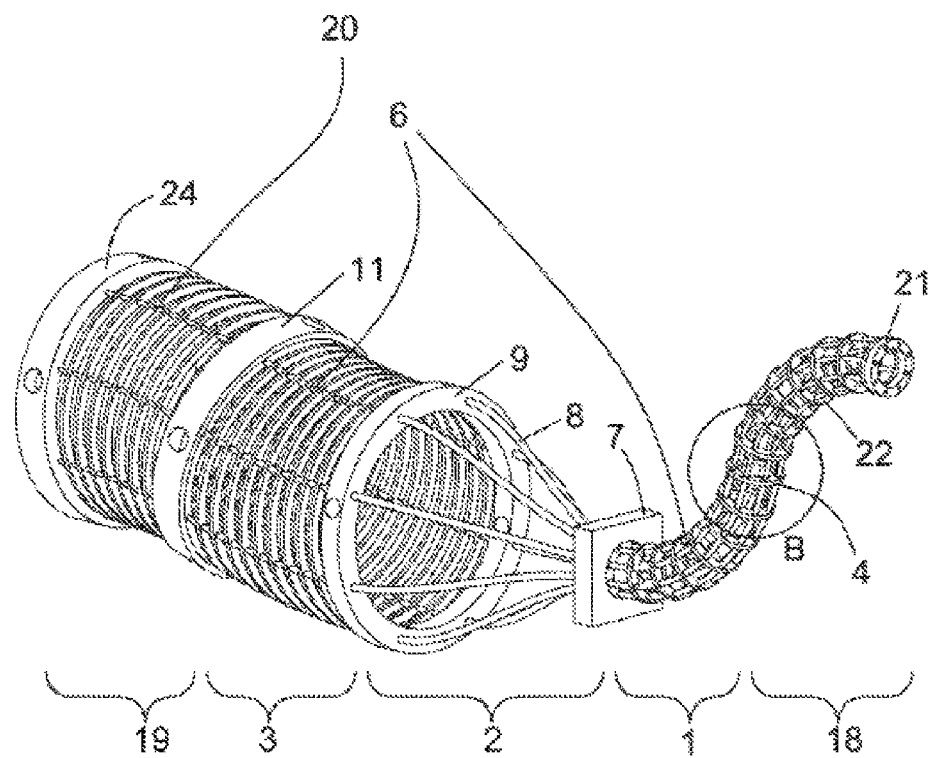
Figure 11B:
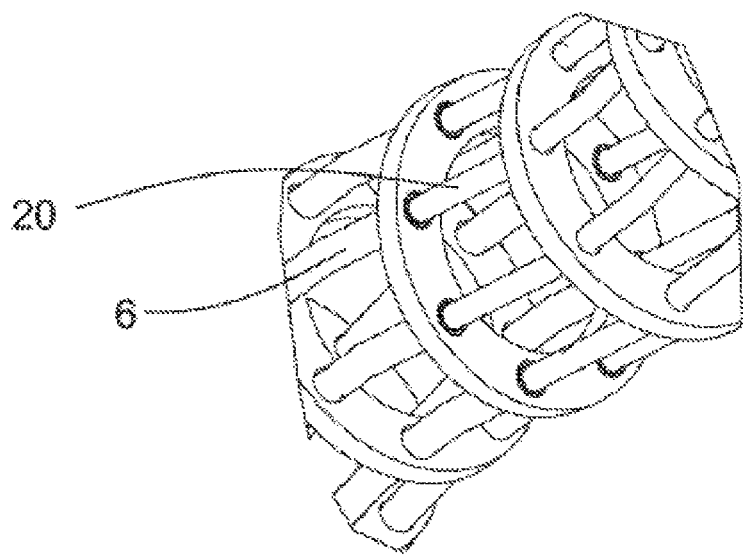

The backbones 6 of the first continuum mechanical structure of the plurality of continuum mechanical structures as shown in FIG. 10 are elastic thin rods. However, the backbones 6 of the first continuum mechanical structure can also be elastic thin tubes. As shown in FIG. 11A and FIG. 11B, when the backbones are elastic thin tubes, the backbones 20 of the second continuum mechanical structure can pass through the backbones 6. In addition, the backbones 6 of the first continuum mechanical structure can also be partially elastic thin rods and partially elastic thin tubes. The number of the cannulae 8 in the connecting structure 2 needs to satisfy the requirement of passage of the backbones 6 of the first continuum mechanical structure and the backbones 20 of the second continuum mechanical structure.

In addition, although the sections of the locking discs and spacer discs and the like in the plurality of continuum mechanical structures as shown in FIG. 10 and FIG. 11 are circular-ring-shaped, the sections can also be any shapes.

Figure 12:
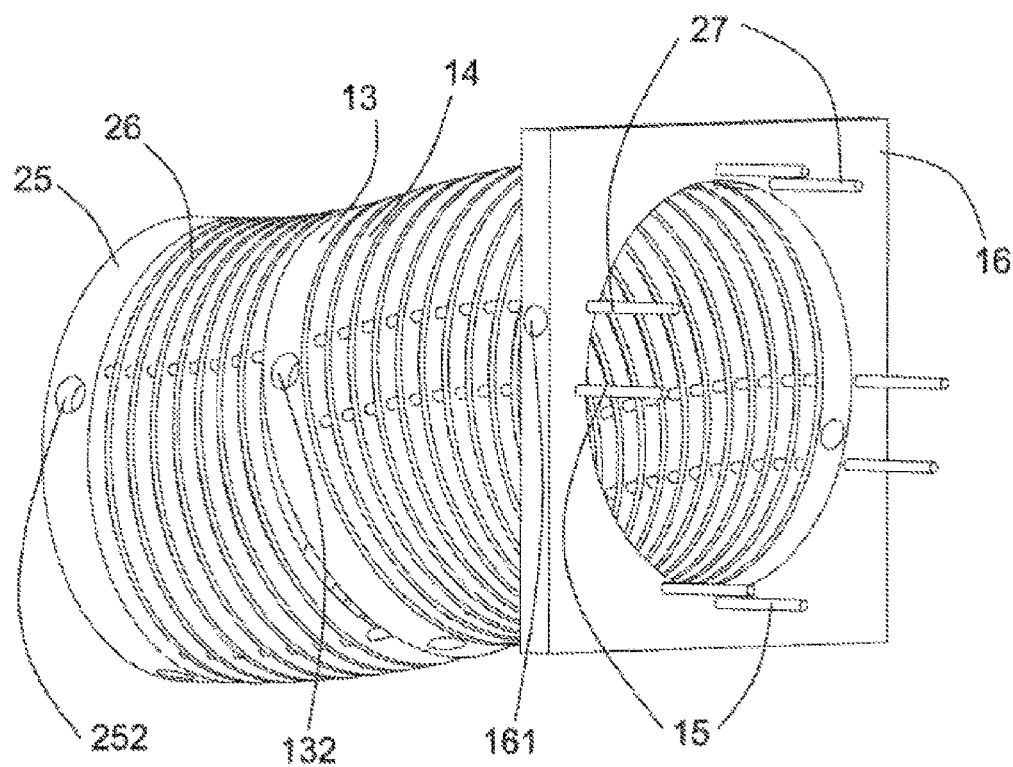
FIG. 12 is a structural schematic view of two driving structures of continuum mechanical structures of the present invention.

FIG. 12 illustrates a stereoscopic view of a driving structure of the flexible continuum mechanical structure according to the present invention. As shown in FIG. 12, the driving structure consists of the second locking disc of the driving structure 25, the second spacer discs of the driving structure 26, the second driving backbones 27, the first locking disc of the driving structure 13, the first spacer discs of the driving structure 14, the first driving backbones 15 and a fixation disc of the driving structure 16. The second driving backbones 27 is fixed on the second locking disc of the driving structure 25 and can freely pass through the second spacer discs of the driving structure 26, the first locking disc of the driving structure 13, the first spacer discs of the driving structure 14 and the fixation disc of the driving structure 16. The first driving backbones 15 is fixed on the first locking disc of the driving structure 13 and can freely pass through the spacer discs of the driving structure 14 and the fixation disc of the driving structure 16. Pin holes 252, pin holes 132 and pin holes 161 used for connecting with the second proximal locking disc 24, the first proximal locking disc 11 and the cannulae fixation plate 9 are respectively formed in the second locking disc of the driving structure 25, the first locking disc of the driving structure 13 and the fixation disc of the driving structure 16.

Figure 13:
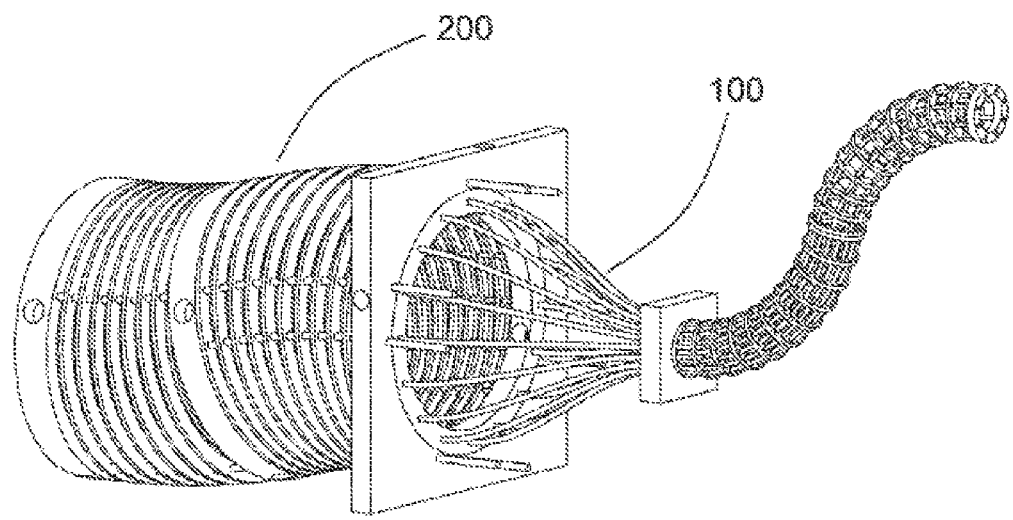
FIG. 13 is a structural schematic view of two ring-section continuum mechanical structures of the present invention after assembled to two driving structures.

FIG. 13 illustrates a structural view of a plurality of flexible continuum mechanical structures in FIG. 10 after being assembled to a plurality of driving structures in FIG. 12. The plurality of flexible continuum mechanical structures are nested in the plurality of driving structures, and the plurality of flexible continuum mechanical structures and the plurality of driving structures are fixed together through pins, etc. After completion of assembly, as shown in FIG. 13, the synchronized pushing and pulling (realized manually or electromechanically) of the second driving backbones 27 and the first driving backbones 15 may enable the second locking disc of the driving structure 25 and the first locking disc of the driving structure 13 to be bent towards any direction, and also may enable the length of the two driving structures to be respectively lengthened and shortened. Since the second locking disc of the driving structure 25, the first locking disc of the driving structure 13 and the fixation disc of the driving structure 16 are respectively connected with the second proximal locking disc 24, the first proximal locking disc 11 and the cannulae fixation plate 9 through pins, the synchronized pushing and pulling of the driving backbones 27, 15 enables the second proximal structure 19 and the first proximal structure 3 to be bent, extended and retracted towards any direction, such that the bending, extension and refraction of the first distal structure 1 and the second distal structure 18 towards any direction are realized.

Figure 14:
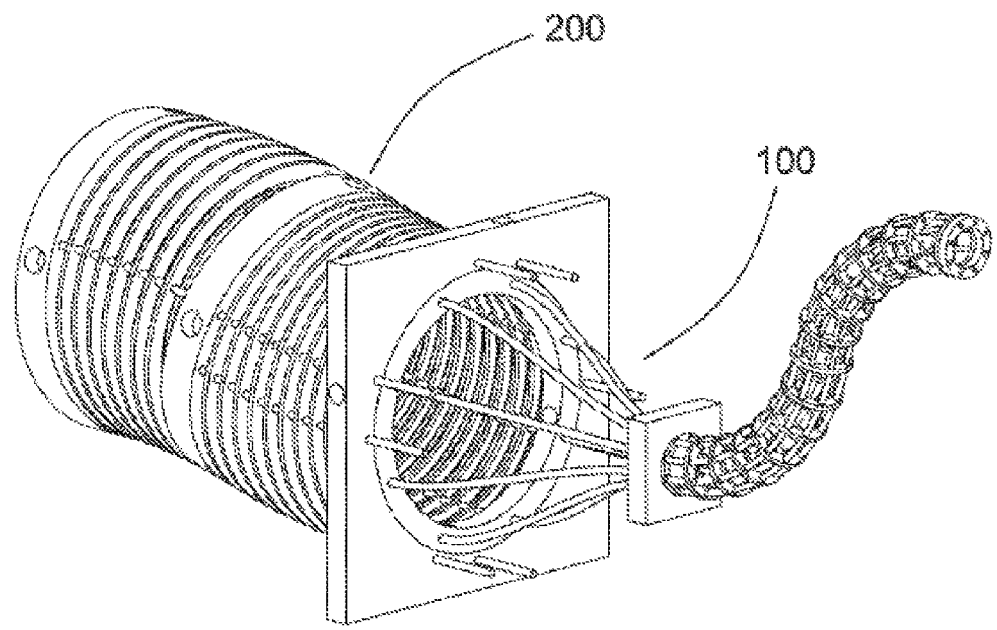
FIG. 14 is a structural schematic view of another two ring-section continuum mechanical structures of the present invention after assembled to two driving structures.

FIG. 14 illustrates a structural view of a plurality of flexible continuum mechanical structures in FIG. 11A after being assembled to a plurality of driving structures in FIG. 12, the drive motion principle of which is consistent with that as shown in FIG. 13, which is not described herein in details.

Embodiment 3

FIGS. 15-16 illustrate a structural view of the third embodiment of the flexible continuum mechanical structure according to the present invention. This embodiment is different from embodiment 2 mainly in that a first distal kinematic chain 1a' and a second distal kinematic chain 18a' are further respectively arranged in the first distal structure 1' and the second distal structure 18' and are respectively used for reinforcing the rigidity, especially the torsional strength of the first distal structure 1' and the second distal structure 18'. The first distal kinematic chain 1a' and the second distal kinematic chain 18a' are respectively kept in compatible kinematic capacity (degree-of-freedom) or in kinematic compatibility with the first distal structure 1' and the second distal structure 18', such that the bending, extension and retraction therewith can be realized. Herein, keeping in compatible kinematic capacity or kinematic compatibility refers to that the implantation of the distal kinematic chains does not obstruct the motion of the distal structures, even though the shape of the distal structures is partially changed.

Specifically, one end of the first distal kinematic chain 1a' is secured to the cannulae fixation plate and the other end is secured to the first distal locking disc 12' of the first distal structure, such that the motion of the first distal structure 1' can drive the first distal kinematic chain 1a' to move correspondingly.

In the embodiment as shown in FIGS. 15-16, the second distal kinematic chain 18a' has a configuration of rotary joint-rotary joint-prismatic joint-rotary joint-rotary joint. Specifically, the second distal kinematic chain 18a' consists of at least six links, wherein one end of a first link 181a1' is secured to a second distal locking disc 181', and the other end is rotatably connected with one end of a second link 181a2' to form a first rotary joint 18aa'; the other end of the second link 181a2' is rotatably connected with one end of a third link 181a3' to form a second rotary joint 18ab'; the other end of the third link 181a3' is retractably connected with one end of a fourth link 181a4' to form a prismatic joint 18ac'; the other end of the fourth link 181a4' is rotatably connected with one end of a fifth link 181a5' to form a third rotary joint 18ad'; the other end of the fifth link 181a5' is rotatably connected with one end of a sixth link 181a6' to form a fourth rotary joint 18ae', and the other end of the sixth link is secured to a first distal locking disc 12'. The arrangement of the rotary joints and the prismatic joint enables the second distal kinematic chain 18a' to have a kinematic capacity compatible with the second distal structure, such that the second distal kinematic chain can bend, extend and retract towards each direction with the second distal structure. In needs to be pointed out that, when more than seven links are arranged, the other end of the sixth link is connected to a seventh link and the last link is secured to the distal locking disc 12'.

In the embodiment as shown in FIGS. 15-16, the first distal kinematic chain 1a' and the second distal kinematic chain 18a' on the first distal structure 1' are the same. However, it should be understood that the structure of the first distal kinematic chain can also be different from that of the second distal kinematic chain. Actually, the structures of the distal kinematic chains can also adopt other structure forms, as long as the rigidity or torsional strength of the distal continuum can be reinforced and the bending, extension and retraction of the distal continuum mechanical structure are not influenced. In another embodiment, flexible shafts are used as the distal kinematic chains. The flexible shafts have higher torsional strength and can be easily bent.

In addition, as shown in FIG. 15, when the connecting structure 2' is longer, retaining rings 2a can be arranged for tying the cannulae 8 into one or more than one bundles to reduce the space occupied by the connecting structure 2. When the connecting structure is shorter, in the first embodiment and the second embodiment as shown in FIGS. 1-14, the retaining rings can also be removed.

Figure 17A:
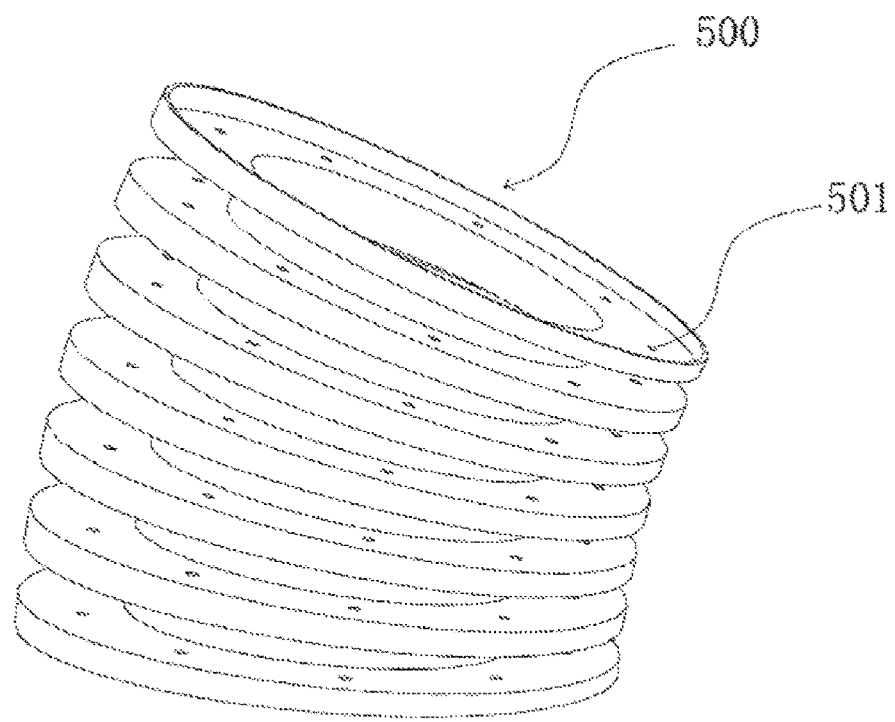
FIGS. 17A and 17B respectively illustrate a stereoscopic view and a sectional view of an embodiment for substituting spacer discs in a distal structure and a proximal structure.
Figure 17B:
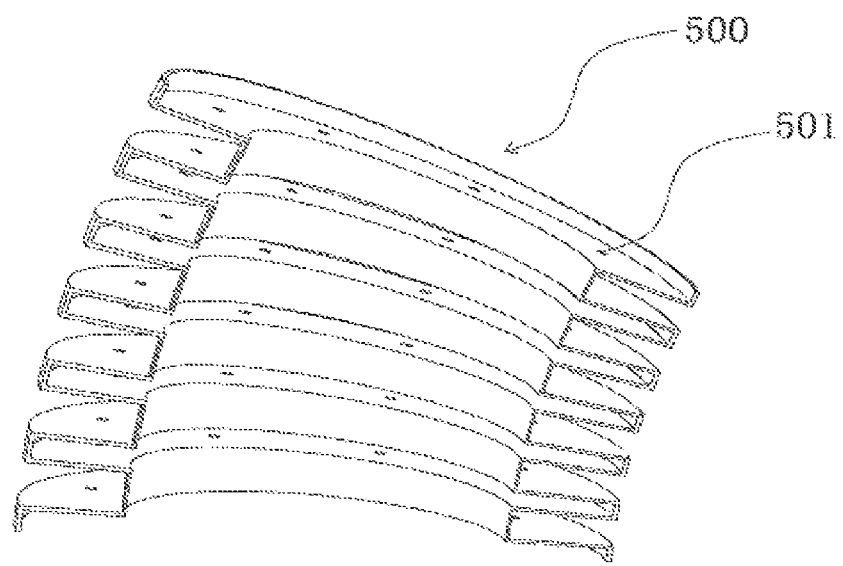
Figure 18:
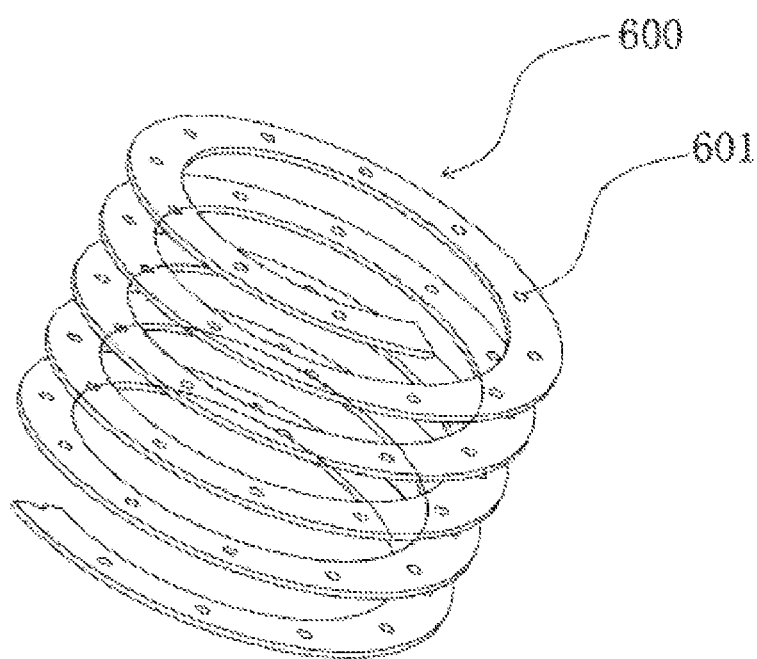
FIG. 18 illustrates a stereoscopic view of another embodiment for substituting spacer discs in a distal structure and a proximal structure.

FIGS. 17A-17B and 18 illustrate two structures for substituting spacer discs in a distal structure and proximal structure. In order to facilitate the description, the structures are called as spacers. The spacers can be extended, retracted and bent, and holes for the penetration of the backbones are formed thereon.

As shown in FIG. 17A and FIG. 17B, the spacer is a bellow 500, and holes 501 for passing the backbones are formed in the outer circumference of the bellow 500. The spacer can also be a spiral spring 600, as shown in FIG. 18, holes 601 for passing the backbones are formed in the spiral spring. The bellow 500 and the spiral spring 600 are made of a material selected from materials which can enable them to be extended, retracted and bent and have the needed torsional strength such that additional distal kinematic chains do not need to be added.

Figure 19:
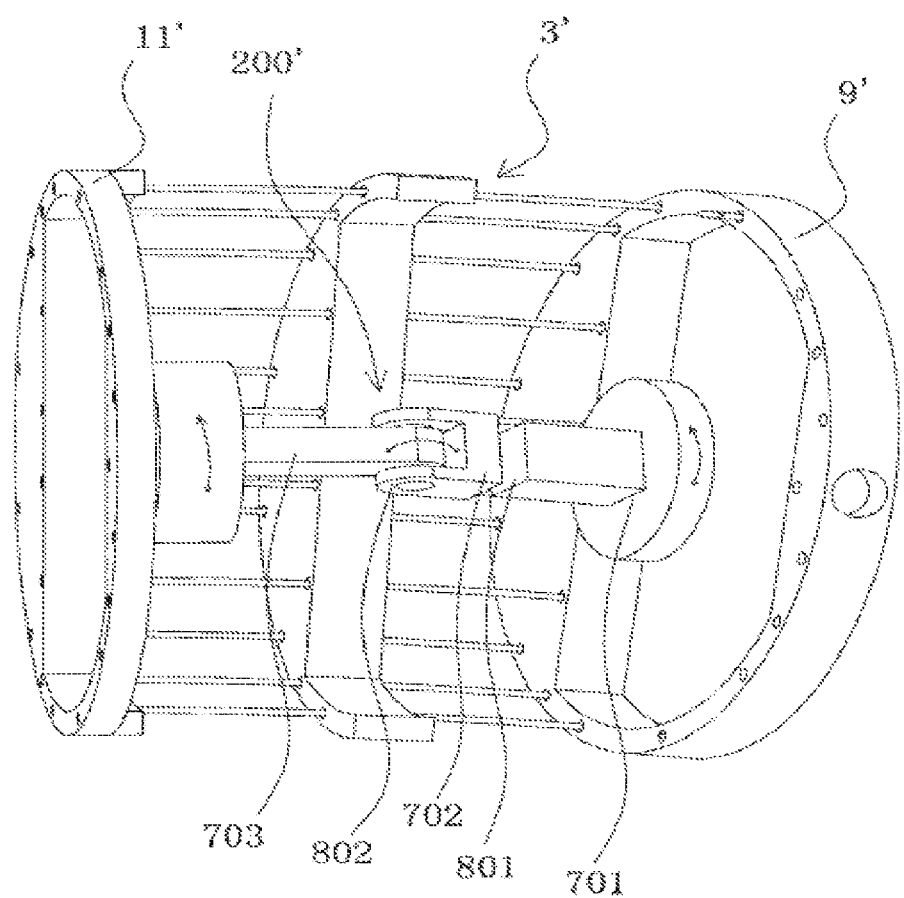
FIG. 19 is a stereoscopic view of another embodiment of the driving structure of the flexible continuum mechanical structure of the present invention.

FIG. 19 illustrates a structural schematic view of another driving structure 200'. For the sake of clarity, FIG. 19 only illustrates the first proximal structure 3' and the driving structure 200' thereof. The structure of the second proximal structure is substantially the same as that of the first proximal structure, which is not described herein in details. In this embodiment, the driving structure 200' is different from the driving structures as shown in FIG. 5 and FIG. 12 in that the driving structure 200' is arranged in the proximal continuum mechanical structure to form a portion of the proximal continuum mechanical structure. However, the driving structures in FIG. 5 and FIG. 12 are separate mechanisms and are different in structure.

Specifically, as shown in FIG. 19, the driving structure 200' consists of a plurality of links, and a prismatic joint and rotary joints which are arranged between the links and between the links and the proximal locking disc, wherein the prismatic joint can drive the first proximal structure 3' to do extension and retraction motions and the rotary joints can drive the first proximal structure to do bending motions.

In a preferred embodiment, the driving structure 200' consists of the link 701, the link 702, the link 703, a rotary joint (not shown in the figure) arranged between the link 701 and the cannulae fixation plate 9', a prismatic joint 801 arranged between the link 701 and the link 702, a rotary joint 802 arranged between the link 702 and the link 703 and a rotary joint (not shown in the figure) arranged between the link 703 and the proximal locking disc 11', wherein the rotary joint arranged between the link 703 and the proximal locking disc 11' is a passive rotary joint, and the other rotary joints are active joints and each are driven by a motor (not shown in the figure) to rotate. Each of the rotary joints can rotate in the direction indicated by the arrow shown in the figure, so as to drive the first proximal structure 3' to do bending motions. The prismatic joint is also driven actively and is driven by the motor (not shown in the figure), so as to do extension and retraction motions in the direction pointed out in the figure to drive the first proximal structure 3' to do extension and retraction motions.

It needs to be pointed out that the specific structure of the driving structure 200' built in the proximal structure can be set according to the needs but is not limited to the structure as shown in the figures, as long as the driving structure can drive the proximal structure to do extension, refraction and bending motions to further drive the distal structure to do corresponding motions.

Moreover, the rotary joints and the prismatic joint of the above-mentioned driving structure 200' can also be arranged to be driven passively and are built in the distal structure to form a distal kinematic chain. Specifically, the distal kinematic chain may comprise a link I, a link II, a link III, a rotary joint arranged between the link I and the cannulae fixation plate or the distal locking disc, a prismatic joint arranged between the link I and the link II, a rotary joint arranged between the link II and the link III and a rotary joint arranged between the link III and the distal locking disc.

The flexible continuum mechanical structure of the present invention realizes the effect of controlling the distal mechanism to be bent and/or extended and retracted towards any direction through proximal operation by using a very simple and compact structure, and has a very wide application range in the medical field and industrial automation equipments.

The better embodiments of the present invention are described above in details. However, it should be understood that, after reading the contents described above in the present invention, one skilled in the art can made various variations or modifications to the present invention. However, such equivalent forms shall fall into the scope defined by claims attached to the present application.

The invention claimed is:

1. A flexible continuum mechanical structure, wherein the flexible continuum mechanical structure comprises:
   a distal structure, comprising distal spacer discs, a distal locking disc, and distal backbones, wherein the distal backbones consist of elastic thin rods or elastic thin tubes;
   a proximal structure, comprising proximal spacer discs, a proximal locking disc, and proximal backbones, wherein the proximal backbones consist of elastic thin rods or elastic thin tubes; and
   a connecting structure, comprising cannulae fixation plates and cannulae, wherein the cannulae fixation plates are fixed to the cannulae,
   where each of the distal backbones is fixedly connected with one corresponding proximal backbone;
   where a distance is kept between the proximal spacer discs and between the proximal spacer discs and the proximal locking disc, and where the proximal spacer discs play roles of limiting positions of the proximal backbones and preventing the proximal backbones from buckling under a pushing force;
   where a distance is kept between the distal spacer discs and between the distal spacer discs and the distal locking disc, the distal spacer discs playing roles of limiting positions of the distal backbones and preventing the distal backbones from buckling under the pushing force;
   where the distal structure is associated with the proximal structure through the connecting structure, and wherein an end of the proximal backbones is fixed on the proximal locking disc, where the proximal backbones pass through the proximal spacer discs, and where an opposite end of the proximal backbones is connected with an end of the corresponding distal backbone in the cannulae of the connecting structure; and
   where the distal backbones pass through the distal spacer discs, and where an opposite end of the distal backbones is fixed on the distal locking disc, such that when the proximal structure is driven to be bent towards any direction, the distal structure is correspondingly bent towards an opposite direction, or when the proximal structure is driven to be extended or retracted, the distal structure is correspondingly retracted or extended.

2. The flexible continuum mechanical structure according to claim 1, wherein a length of the distal and proximal backbones is measurable, estimable, or constant.

3. The flexible continuum mechanical structure according to claim 1, wherein the distal locking disc and the distal spacer discs and the proximal locking disc and the proximal spacer discs respectively have a same through hole arrangement and are rigid disc-shaped structures.

4. The flexible continuum mechanical structure according to claim 1, wherein the connecting structure consists of more than three cannulae and more than two cannulae fixation plates, an end of the distal backbones of the flexible continuum mechanical structure being connected with an end of the corresponding proximal backbones inside the cannulae, where the opposite end of the distal backbones protrudes into the distal structure, passes through the distal spacer discs and is fixed on the distal locking disc, and where the opposite end of the proximal backbones protrudes into the proximal structure, passes through the proximal spacer discs and is fixed on the proximal locking disc.

5. The flexible continuum mechanical structure according to claim 1, wherein the flexible continuum mechanical structure is formed by more than two proximal structures and more than two distal structures through serial connection to obtain higher motion dexterity.

6. The flexible continuum mechanical structure according to claim 1, wherein the connecting structure has two cannulae fixation plates, and wherein two ends of the cannulae are respectively secured to the two cannulae fixation plates.

7. The flexible continuum mechanical structure according to claim 1, wherein:
   a length of the distal and proximal backbones is measurable, estimable, or constant; and
   when the proximal structure is driven to be bent or extended and retracted towards any direction, the distal structure is bent or extended and retracted towards an opposite direction.

8. The flexible continuum mechanical structure according to claim 1, wherein the proximal locking disc is in a shape of a ring, and a plurality of pin holes along a radial direction are formed in an outer circumferential side of the ring and are used for connecting the proximal structure to a driving structure.

9. The flexible continuum mechanical structure according to claim 1, wherein a number of the distal backbones is greater than or equal to three.

10. The flexible continuum mechanical structure according to claim 1, wherein a cannulae fixation plate connected with the distal structure is a rectangular plate part and a cannulae fixation plate connected with the proximal structure is a circular ring part.

11. The flexible continuum mechanical structure according to claim 1, wherein a cannulae fixation plate connected with the distal structure is a rectangular plate part and a cannulae fixation plate connected with the proximal structure is disc-shaped.

12. The flexible continuum mechanical structure according to claim 1, wherein a cannulae fixation plate connected with the distal structure is smaller than a cannulae fixation plate connected with the proximal structure.

13. The flexible continuum mechanical structure according to claim 1, wherein the distal backbones and proximal backbones bear a pulling force or a pushing force.

14. A flexible continuum mechanical structure, wherein the flexible continuum mechanical structure comprises:
    a distal structure, comprising distal spacer discs, a distal locking disc, and distal backbones, wherein the distal backbones consist of elastic thin rods or elastic thin tubes;
    a proximal structure, comprising proximal spacer discs, a proximal locking disc, and proximal backbones, wherein the proximal backbones consist of elastic thin rods or elastic thin tubes;
    a connecting structure, comprising cannulae fixation plates and cannulae, wherein the cannulae fixation plates are fixed to the cannulae; and
    a driving structure, used for driving the proximal structure to move and consisting of a locking disc of the driving structure, spacer discs of the driving structure, driving backbones and a fixation disc of the driving structure, an end of the driving backbones being secured to the locking disc of the driving structure and sequentially passing through the spacer discs of the driving structure and the fixation disc of the driving structure;
    where each of the distal backbones is fixedly connected with one corresponding proximal backbone;
    where a distance is kept between the proximal spacer discs and between the proximal spacer discs and the proximal locking disc, and the proximal spacer discs play roles of limiting positions of the proximal backbones and preventing the proximal backbones from buckling under a pushing force;
    where a distance is kept between the distal spacer disc and between the distal spacer discs and the distal locking disc, and the distal spacer discs play roles of limiting positions of the distal backbones and preventing the distal backbones from buckling under the pushing force;
    where the distal structure is associated with the proximal structure through the connecting structure, and wherein an end of the proximal backbones is fixed on the proximal locking disc, the proximal backbones pass through the proximal spacer discs, and wherein an opposite end is connected with an end of the corresponding distal backbones in the cannulae of the connecting structure, where the distal backbones pass through the distal spacer discs, and where an opposite end of the distal backbones is fixed on the distal locking disc; and
    where the driving structure is connected with the proximal structure, such that when the driving backbones are driven, the driving structure drives the proximal structure to be bent towards any direction and the distal structure is correspondingly bent towards an opposite direction, or when the driving structure drives the proximal structure to be extended or retracted, the distal structure is correspondingly retracted or extended.

15. The flexible continuum mechanical structure according to claim 14, wherein the locking disc of the driving structure is fixedly connected with the proximal locking disc, and the fixation disc of the driving structure is fixedly connected with the cannulae fixation plates of the connecting structure, such that when the driving structure is driven to be bent or extended and retracted towards any direction, the proximal structure is correspondingly bent or extended and retracted towards a same direction.

16. The flexible continuum mechanical structure according to claim 14, wherein a number of the driving backbones is greater than or equal to three, and corresponding pushing and pulling motions of the driving backbones are realized manually or through an automatically controlled electromechanical system.

17. The flexible continuum mechanical structure according to claim 14, wherein one or more driving structures are serially connected to form a plurality of driving structures to realize actuation of the flexible continuum mechanical structure formed by a plurality of proximal structures and distal structures through serial connection.

18. The flexible continuum mechanical structure according to claim 14, wherein the proximal spacer discs and the distal spacer discs are ring-shaped, and a plurality of backbone holes for passing the distal and proximal backbones are formed in the rings.

19. The flexible continuum mechanical structure according to claim 14, wherein a plurality of pin holes along a radial direction are formed in an outer circumferential side of the cannulae fixation plate of the connecting structure, close to the proximal structure, and are used for connecting with the driving structure.

20. The flexible continuum mechanical structure according to claim 14, wherein the cannulae have any shape, rigidity or flexibility, but a length of the cannulae is measurable, estimable, or constant.

21. The flexible continuum mechanical structure according to claim 14, wherein the proximal structure is assembled inside of the driving structure.

22. A flexible continuum mechanical structure, wherein the flexible continuum mechanical structure comprises:
    a distal structure, comprising distal spacer discs, a distal locking disc, and distal backbones, wherein the distal backbones consist of elastic thin rods or elastic thin tubes;
    distal kinematic chains, built in the distal structure and used for changing a rigidity of the distal structure, and the distal kinematic chains are kept in kinematic compatibility with the distal structure;
    a proximal structure, comprising proximal spacer discs, a proximal locking disc, and proximal backbones, wherein the proximal backbones consist of elastic thin rods or elastic thin tubes; and
    a connecting structure, comprising cannulae fixation plates and cannulae, wherein the cannulae fixation plates are fixed to the cannulae,
    where each of the distal backbones is fixedly connected with one corresponding proximal backbone;

where a distance is kept between the proximal spacer discs and between the proximal spacer discs and the proximal locking disc, and the proximal spacer discs play roles of limiting positions of the backbones and preventing the proximal backbones from buckling under a pushing force;

where a distance is kept between the distal spacer discs and between the distal spacer discs and the distal locking disc, and the distal spacer discs play roles of limiting positions of the distal backbones and preventing the distal backbones from buckling under the pushing force; and where the distal structure is associated with the proximal structure through the connecting structure, wherein an end of the proximal backbones is fixed on the proximal locking disc, the proximal backbones pass through the proximal spacer discs, and where an opposite end of the proximal backbones is connected with an end of the corresponding distal backbones in the cannulae of the connecting structure;

where the distal backbones pass through the distal spacer discs, and where an opposite end of each of the distal backbones is fixed on the distal locking disc, such that when the proximal structure is driven to be bent towards any direction, the distal structure is correspondingly bent towards an opposite direction, or when the proximal structure is driven to be extended or retracted, the distal structure is correspondingly retracted or extended.

23. The flexible continuum mechanical structure according to claim 22, wherein retaining rings are further arranged on the connecting structure and are used for dividing the cannulae of the connecting structure into a plurality of bundles.

24. The flexible continuum mechanical structure according to claim 22, wherein:

the distal kinematic chains consist of more than six links;

an end of a first link is secured to the cannulae fixation plates of the connecting structure, and an opposite end of the first link is rotatably connected with an end of a second link to form a first rotary joint;

an opposite end of the second link is rotatably connected with an end of a third link to form a second rotary joint;

an opposite end of the third link being retractably connected with an end of a fourth link to form a prismatic joint; an opposite end of the fourth link is rotatably connected with an end of a fifth link to form a third rotary joint; an opposite end of the fifth link is rotatably connected with an end of a sixth link to form a fourth rotary joint;

an opposite end of the sixth link is secured to the distal locking disc, or the sixth link is connected to a seventh link and the seventh link is secured to the distal locking disc; and an arrangement of the rotary joints and the prismatic joint enables the distal kinematic chains to be kept in kinematic compatibility with the distal structure, such that the distal kinematic chains can be bent, extended, and retracted towards each direction with the distal structure.

25. A flexible continuum mechanical structure, wherein the flexible continuum mechanical structure comprises:

a distal structure, comprising distal spacer discs, a distal locking disc, and distal backbones, wherein the distal backbones consist of elastic thin rods or elastic thin tubes;

distal kinematic chains, built in the distal structure and used for changing a rigidity of the distal structure, the distal kinematic chains kept in kinematic compatibility with the distal structure;

a proximal structure, comprising proximal spacer discs, a proximal locking disc, and proximal backbones, wherein the proximal backbones consist of elastic thin rods or elastic thin tubes;

a connecting structure, comprising cannulae fixation plates and cannulae, wherein the cannulae fixation plates are fixed to the cannulae; and a driving structure, built in the proximal structure, wherein the driving structure comprises a link I, a link II, and a link III arranged serially, wherein each of the distal backbones is fixedly connected with one corresponding proximal backbone;

where a distance is kept between the proximal spacer discs and between the proximal spacer discs and the proximal locking disc, where the proximal spacer discs play roles of limiting positions of the proximal backbones and preventing the proximal backbones from buckling under a pushing force;

where a distance is kept between the distal spacer discs and between the distal spacer discs and the distal locking disc, where the distal spacer discs play roles of limiting positions of the distal backbones and preventing the distal backbones from buckling under the pushing force;

where the distal structure is associated with the proximal structure through the connecting structure, and wherein an end of the proximal backbones is fixed on the proximal locking disc, the proximal backbones pass through the proximal spacer discs, and where an opposite end of the proximal backbones is connected with an end of the corresponding distal backbones in the cannulae of the connecting structure; and where the distal backbones pass through the distal spacer discs, and where an end of the distal backbones is fixed on the distal locking disc, such that when the proximal structure is bent towards any direction under the actuation of the driving structure, the distal structure is correspondingly bent towards an opposite direction, or when the proximal structure is driven to be extended or retracted, the distal structure is correspondingly retracted or extended.

26. The flexible continuum mechanical structure according to claim 25, wherein the driving structure consists of a plurality of links and a prismatic joint and rotary joints which are arranged between the links and between the links and the proximal locking disc, the prismatic joint drives the proximal structure to do extension and retraction motions, and the rotary joints can drive the proximal structure to do bending motions.

27. The flexible continuum mechanical structure according to claim 25, wherein a rotary joint is arranged between the link I and the cannulae fixation plates of the connecting structure, a prismatic joint is arranged between the link I and the link II, a rotary joint is arranged between the link II and the link III, and a rotary joint is arranged between the link III and the proximal locking disc, wherein the rotary joint arranged between the link III and the proximal locking disc is a passive rotary joint, and the other rotary joints and the prismatic joint are active joints and are driven to move by motors so as to drive the proximal structure to do bending motions or extension and retraction motions.

28. The flexible continuum mechanical structure according to claim 25, wherein the distal spacers and the proximal spacers are bellows or spiral springs, and backbone holes for passing the distal and proximal backbones are respectively formed in the bellows or the spiral springs.

* * * * *